United States Patent [19]
Johnson

[11] Patent Number: 5,405,941
[45] Date of Patent: Apr. 11, 1995

[54] MEKK PROTEIN, CAPABLE OF PHOSPHORYLATING MEK

[75] Inventor: Gary L. Johnson, Boulder, Colo.

[73] Assignee: National Jewish Center For Immunology and Respiratory Medicine, Denver, Colo.

[21] Appl. No.: 49,254

[22] Filed: Apr. 15, 1993

[51] Int. Cl.⁶ ............................................. C07K 13/00
[52] U.S. Cl. .................................. 530/350; 435/69.1; 536/23.1
[58] Field of Search ....................... 435/69.1; 530/350; 536/23.1

[56] References Cited

PUBLICATIONS

Kolch et. al., "Raf-1 Protein Kinase is Required for Growth of Induced NIH/3T3 Cells", pp. 426–428, 1991, NATURE, vol. 349, Jan. 31.

L'Allemain et al., "p42/Mitogen–Activated Protein Kinase as a Converging Target for Different Growth Factor Signaling Pathways: Use of Pertussis Toxin as a Discrimination Factor", pp. 675–684, 1991, Cell Reg., vol. 2, Aug.

Leberer et. al., "The Protein Kinase Homologue Ste20p is Required to Link the Yeast Pheromone Response G-protein βγ Subunits to Downstream Signalling Components", pp.4815–4824, 1992, EMBO J., vol. 11.

Qureshi et. al., "An Inhibitory Mutant of c-Raf-1 Blocks v-Src-induced Activation of the Egr-1 Promoter", pp. 20594–20597, 1991, J. Biol. Chem., vol. 226, No. 31, Nov. 5.

Stevenson et. al., "Constitutive Mutants of the Protein Kinase STE11 Activate the Yeast Pheromone Respone Pathway in the Absence of the G Protein", pp. 1293–1304, 1992, GENES & Dev., vol. 6.

Tamaki et. al., "Surface Immunoglobulin–mediated SIgnal Transduction Involves Rapid Phosphorylation and Activation of the Protooncogene Product Raf-1 in Human B-Cells", pp. 566–570, 1992, Cancer Res., vol. 52, Feb. 1.

Chaleff et al., Mol. & Cellular Biology, vol. 5, 1878, 1985.

Wang et al., Mol & Cellular Biology, vol. 11, 3554, 1991.

Crews et al., Science, vol. 258, 478, 1992.

*Primary Examiner*—Robert J. Hill, Jr.
*Assistant Examiner*—Sally P. Teng
*Attorney, Agent, or Firm*—Sheridan Ross & McIntosh

[57] ABSTRACT

The isolated nucleic acid sequence for MEKK, the MEKK amino acid sequence and protein, antibodies to MEKK, and methods for using such sequences, proteins and antibodies are described. The amino acid sequence of MEKK (MEK kinase), was elucidated from a cDNA sequence encoding a protein of 672 amino acid residues (73 kilodaltons). When MEKK is expressed, it phosphorylates and activates MEK. Phosphorylation and activation of MEK by MEKK is independent of Raf, a growth factor regulated protein kinase that also phosphorylates MEK. Thus, MEKK and Raf converge at MEK in the protein kinase network mediating the activation of MAPKs by hormones, growth factors, and neurotransmitters.

19 Claims, 14 Drawing Sheets

```
tacactccttgccacagtctgcagaaagaatcaaacttcagagactcctcc         52
ggccagttgtagacactatctctacagtgtctgttgcaagtgtgcagatccaacagccgcacg   104
agtcagctgtccatatctctacagtgctgctgaacttaaagctggtccatcaagggccaagcaggag 156
agctggcggttgggagagaatactcttaaagctggttccatcggggttggtgg       208
tgtcgattacgtcttaagttgtatcctgtcctgttgaaaccaagctgaatcaaacaac    260
tggcaagaactgctgggtcgcgctcctataccttatagacaggttgctgttggaat     312
ttcctgctgaattctctatcctcatattgtcagtactgatgtctcacaagctga      364
gcctgtttgaaatcaggtacaagaagctgctccctcctttaaccttgccttg       416
aatccattgacaattcccactcg                       439
atgqttggcaagctctctggaggatatatctgagctctgccaggatg gtg         490
 M   V   G   K   L   S   R   R   I   Y   L   S   A   R   M   V    2 acc gca gtg ccc gct gtg tcc aag ctg gta acc atg                529
 T   A   V   P   A   V   S   K   L   V   T   M                 15 ctt aat gct tct ggc tcc acc cac ttc acc agg atg cgc             568
 L   N   A   S   G   S   T   H   F   T   R   M   R             28 cgg cgt atg ctg gct atc gcg gat gtg gta gaa att gcc             607
 R   R   M   L   A   I   A   D   V   V   E   I   A             41 gag gtc atc cag ctg ggt gtg gag gac act gtg gat ggg             646
 E   V   I   Q   L   G   V   E   D   T   V   D   G             54 cat cag gac cag tta cag gcc gtg gcc acc agc tgt                685
 H   Q   D   Q   L   Q   A   V   A   T   S   C                 67 cta gaa aac agc tcc ctt gag cac gtc cat aga gag                724
 L   E   N   S   S   L   E   H   V   H   R   E                 80 aaa act gga aaa gga att tct gct agt ctg agt gcc                763
 K   T   G   K   G   I   S   A   S   L   S   A                 93 agc tcg gag gac ctt tct gac aca acg ctg ggc gtc tct             802
 S   S   E   D   L   S   D   T   T   L   G   V   S            106 gta gga ctt caa cta tca aaa ggc aga caa cca aag                841
 V   G   L   Q   L   S   K   G   R   Q   P   K                119 cca gcg gtt caa aca ccc cac agt cag tgt                     880
 P   A   V   Q   T   P   H   S   Q   C                       132 ttg aac tcc cct ttg tct cat gct caa tta atg ttc                919
 L   N   S   P   L   S   H   A   Q   L   M   F                145
```

| | | | | | | | | | | | | pos | aa |
|---|---|---|---|---|---|---|---|---|---|---|---|---|---|
| cca P | gca A | cca P | tca S | gcc A | cct P | tgt C | tcc S | tct S | gcc A | ccg P | tct S | gtc V | 958 / 158 |
| cca P | gat D | att I | tct S | aag K | cac H | aga R | ccc P | cag Q | gca A | ttt F | gtt V | ccc P | 997 / 171 |
| tgc C | aaa K | ata I | cct P | tcc S | gca A | tct S | cct P | cag Q | aca T | gtt V | cgc R | aag K | 1036 / 184 |
| ttc F | tct S | cta L | caa Q | ttc F | cag Q | agg R | aac N | cag Q | aca T | cag Q | cac H | cga R | 1075 / 197 |
| gac D | tca S | gac D | cag Q | ctc L | cag Q | cca P | gtc V | ttc F | tct S | gaa E | tca S | aga R | 1114 / 210 |
| ccc P | cca P | ccc P | cag Q | agt S | tcc S | aac N | cac H | agg R | act T | cag Q | cca P | tcc S | 1153 / 223 |
| cga R | ccc P | gtt V | tcc S | ggc G | cca P | ata I | aca T | agc S | aaa K | aag K | cta L | gcc A | 1192 / 236 |
| aca T | aaa K | agt S | ggc G | atg M | aac N | ctt L | gat D | agg R | ctg L | ggg G | cca P | tcc S | 1231 / 249 |
| agg R | tgt C | gac D | atg M | agc S | aca T | ttt F | ggc G | gat D | ggc G | aag K | agt S | ggc G | 1270 / 262 |
| aac N | gcc A | gtc V | gac D | ccc P | agc S | agg R | gag E | gac D | gag E | ggg G | aac N | ccg P | 1309 / 275 |
| gtg V | gag E | gtc V | ata I | tgc C | agg R | gac D | ctt L | gat D | gtg V | agt S | acc T | ctc L | 1348 / 288 |
| aac N | tcc S | gac D | aag K | gag E | gac D | ctt L | ctt L | gtc V | aac N | aac N | gag E | cct P | 1387 / 301 |
| tca S | agt S | agc S | atc I | aca T | gcc A | act T | ttc F | aat N | gca A | gaa E | acc T | gcc A | 1426 / 314 |
| gtc V | ctc L | gac D | acg T | gaa E | aat N | cat H | caa Q | aaa K | tgc C | gat D | tac Y | aag K | 1465 / 327 |
| aaa K | gac D | gtc V | ccg P | gta V | aat N | cat H | gag E | aaa K | aaa K | gcg A | gaa E | atg M | 1504 / 340 |
| atg M | gaa E | gct A | gaa E | gag E | gag E | gag E | gct A | gcg A | atc I | tta L | gcc A | atg M | 1543 / 353 |

FIG. 1B

```
                                                                                              1582
gcg atg tca gcg tct cag gat gcc ctc ccc atc gtc cct                                            366
 A   M   S   A   S   Q   D   A   L   P   I   V   P
                                                                                              1621
cag ctg cag gtg cag aat gga act gat gat ctt atc att                                            379
 Q   L   Q   V   Q   N   G   T   D   D   L   I   I
                                                                                              1660
cag cag gac aca gaa gaa gga gaa cca att atc acc aaa                                            392
 Q   Q   D   T   E   E   G   E   P   I   I   T   K
                                                                                              1699
gcg aaa cag cct ata aga aga gac gca gga tgg cat ctg aaa                                        405
 A   K   Q   P   I   R   R   D   A   G   W   H   L   K
                                                                                              1738
ggc cag caa gtg tac ctc ggg act ttt gct gag tcc tgt tac                                        418
 G   Q   Q   V   Y   L   G   T   F   A   E   S   C   Y
                                                                                              1777
caa cag gca gat gtg gga ttt aca gca ggg aac agg atg gct gtg                                    431
 Q   Q   A   D   V   G   F   T   A   G   N   R   M   A   V
                                                                                              1816
aaa cag cag acg tac tac gag gaa tcc atg tcc cag                                                444
 K   Q   Q   T   Y   Y   E   E   S   M   S   Q
                                                                                              1855
gag gag gag gtg gtg gag aga gaa atc cgg atc atg                                                457
 E   E   E   V   V   E   R   E   I   R   I   M
                                                                                              1894
atg gag cac ctc tgc agg tta aac ttc atc ctc                                                    470
 M   E   H   L   C   R   L   N   F   I   L
                                                                                              1933
ggg gcc acg aag tgc gga gag gag ctc aac tac agt att                                            483
 G   A   T   K   C   G   E   E   L   N   Y   S   I
                                                                                              1972
gag gcc ttc gca gga tcc cat gtt gct tac aaa act                                                496
 E   A   F   A   G   S   H   V   A   Y   K   T
                                                                                              2011
tac gaa ctg tta att gga aaa gtc tcc aaa tac S
 Y   E   L   L   I   G   K   V   S   K   Y   E   Y
                                                                                              2050
tct gag cgt cac cag acc aaa ctg cat aac gag                                                    522
 S   E   R   H   Q   T   K   L   H   N   E
                                                                                              2089
aac cag cac atc agc gac gac aga cgt att ctg gca gac                                            535
 N   Q   H   I   S   D   D   R   R   I   L   A   D
                                                                                              2128
ctc att gac gct ctt cag agg tca gca ttg acc                                                    548
 L   I   D   A   L   Q   R   S   A   L   T
                                                                                              2167
ttt gga gct acc agg ttg gtg                                                                    561
 F   G   A   T   R   L   V
```

FIG. 1C

```
gca gga gag ttc cag gga cag tta ctg ggg aca att gca       2206
 A   G   E   F   Q   G   Q   L   L   G   T   I   A        574
ttc atg gcg cct gag gtc cta aga ggt cag tat ggt           2245
 F   M   A   P   E   V   L   R   G   Q   Y   G           587
agg agc tgt gat gta tgg agt cca gtt ggc gcc att ata       2284
 R   S   C   D   V   W   S   P   V   G   A   I   I       600
gaa atg gct tgt gca aaa cca tgg aat gca gaa aaa           2323
 E   M   A   C   A   K   P   W   N   A   E   K           613
cac tcc aat cat ctc gcc ttg ata ttt aag att gct agc       2362
 H   S   N   H   L   A   L   I   F   K   I   A   S       626
gca act gca ccg tcc atc ccg tca cac ctg tcc ccg           2401
 A   T   A   P   S   I   P   S   H   L   S   P           639
ggt ctg cgc gac gtg gcc gtg cgc tta gaa gag ctt cag       2440
 G   L   R   D   V   A   V   R   L   E   E   L   Q       652
cct cag gac cgg cct acc ccg tcc aga gag ctg aaa cat       2479
 P   Q   D   R   P   T   P   S   R   E   L   K   H       665
ccg gtc cgt ttc acg tgg tag                               2503
 P   V   R   F   T   W   *                                672
ttaattgttcagatcagtctctaatggagacaggatatcgaaccgggagagag     2555
aaaagagaacttgtgggccatgcgaccatgccgctaaccgcagccctcacgccactg 2607
aacagccagaaacggggccagcgtacctaagctctacagatcagtgtgattgaca   2659
aatcatgaccctgtacctgccttttcacaggaacatctacagactgtgatgcagctcgtgcagg 2711
aactgcacaccgtgcatgactgactaaagaacagaagcatatcaacatgcccgccacttttgg 2763
tggagtttgcatgactagtattaccagtgtcaagatgtacatccactgtgtttgttttgcagtt 2815
tttcagctaatcagtcccagatgtgtccagatgtcaagatgtttttgttttttcagtt       2867
ctcagactgtgtccagatgtcaagatgtgtttttgttttttcgatgcaaatgtactgatgt    2919
ccctcagctgtctgctctatttcttggatcaaagctgaaaattgtactgtgtaa          2971
aatattctatttttcttgttttaatgttattgtgtactcgaattgtaaataacgtcta      3023
ttattttgtgttattccagtttctactacctcaggtgtcctatagatttttcttc         3075
ctgcgtgttattcactctcagaatgaaattctacgtgctgtgactatgactc            3127
taccaaagttcactctcagaatgaaattctacgtgctgtgactatgactc              3179
ctaagacttccaggcttaaggctaactcctattagcaccttactactatgtaa            3231
gcaaatgctacaaaaaaaaaaaaaaaaa                                     3260
```

FIG. ID

MEKK PROTEIN, CAPABLE OF PHOSPHORYLATING MEK

This invention was made in part with government support under USPHS Grants DK37871, GM30324 and CA58187, all awarded by the National Institutes of Health. The government has certain rights to this invention.

FIELD OF THE INVENTION

This invention relates to isolated MEK kinase kinase nucleic acid sequences, substantially pure MEKK proteins and methods involved in the regulation and use of MEKK and MED and MAPK enzymes.

BACKGROUND OF THE INVENTION

Mitogen-activated protein kinase (MAPKs) (also called extracellular signal-regulated kinases or ERKs) are rapidly activated in response to ligand binding by both growth factor receptors that are tyrosine kinases (such as the epidermal growth factor (EGF) receptor) and receptors that are coupled to heterotrimeric guanine nucleotide binding proteins (G proteins) such as the thrombin receptor. The MAPKs appear to integrate multiple intracellular signals transmitted by various second messengers. MAPKs phosphorylate and regulate the activity of enzymes and transcription factors including the EGF receptor, Rsk 90, phospholipase A2, arachidonic acid metabolites, c-Myc, and perhaps c-Jun. Although the rapid activation of MAPKs by receptors that are tyrosine kinases is dependent on Ras, G protein-mediated activation of MAPK appears to occur predominantly through pathways independent of Ras.

Complementation analysis of the pheromone-induced signaling pathway in yeast has defined a protein kinase system that controls the activity of Spk1 and Fus3-Kss1, the *Schizosaccharomyces pombe* and *Saccharomyces cerevisiae* homologs of MAPK (see for example, B. R. Cairns et al., Genes and Dev. 6, 1305 (1992); B. J. Stevenson et al., Genes and Dev. 6, 1293 (1992); S. A. Nadin-Davis et al., EMBO J. 7, 985 (1988); Y. Wang et al., Mol. Cell. Biol. 11, 3554 (1991). In *S. cerevisiae*, the protein kinase Ste7 is the upstream regulator of Fus3-Kss1 activity; the protein kinase Ste11 regulates Ste7. The *S. pombe* gene products Byr1 and Byr2 are homologous to Ste7 and Ste11, respectively. The MEK (MAPK Kinase or ERK Kinase) or MKK (MAP Kinase Kinase) enzymes are similar in sequence to Ste7 and Byr1. The MEKs phosphorylate MAPKs on both tyrosine and threonine residues which results in activation of MAPK. The mammalian serine/threonine protein kinase Raf phosphorylates and activates MEK, which leads to activation of MAPK. Raf is activated in response to growth factor receptor tyrosine kinase activity and therefore Raf may activate MAPK in response to stimulation of membrane-associated tyrosine kinases. Raf is unrelated in sequence to Ste11 and Byr2. Thus, Raf may represent a divergence in mammalian cells from the pheromone-responsive protein kinase system defined in yeast. Cell and receptor specific differences in the regulation of MAPKs suggest that other Raf independent regulators of mammalian MEKs exist.

SUMMARY OF THE INVENTION

The present invention is directed to a novel gene, denoted MEKK or mammalian MEK kinase. The regulation of MEKK is useful in various therapeutic applications that involve differentiation and mitogenesis. In particular, the present invention is directed to the regulation of mitogen-activated protein kinases (MAPKs) which the present inventor has discovered is activated by MEKK. Because MAPKs are known to phosphorylate and regulate the activity of enzymes and/or transcription factors, the present invention is directed to the regulation of such activities either through manipulation of the nucleic acid sequences encoding MEKK and/or through administration of MEKK to desired cell populations. The present invention is also directed to the dual regulation by Raf and MEKK to effect desired levels of MAPK activity and to alter typical responses to ligand binding by both growth factor receptors, such as tyrosine kinases, and receptors that are coupled to G proteins, such as the thrombin receptor. The present invention is therefore directed to substantially pure MEKK, to isolated nucleic acid sequences encoding MEKK, to host cells transformed with the MEKK gene, and to antibodies to the MEKK protein. The present invention is further directed to gene therapy using the MEKK gene to regulate responses to ligand binding by growth factor receptors and G protein-linked receptors.

One aspect of the present invention involves the inactivation of MEKK to inhibit metastasis, various forms of cancer, autoimmune diseases, allergic responses and inflammatory responses. Another aspect involves the stimulation of MEKK production to facilitate wound healing activities. The present invention is therefore useful in controlling the activity of neutrophil, macrophage and basophil cells in inflammatory responses in the lung and various other tissues. The present invention is useful in affecting pathways regulated by platelet activiting factors, and thrombin receptors. It also finds application in the inhibition of angiogenesis and certain kinds of tumors, particularly lung carcinomas and other epithelial carcinomas and the treatment of smooth muscle and arterial tissues. Additionally, the present invention can be used to inhibit chemotactic responses of neutrophils and macrophages, as well as to ameliorate allergic responses.

The present invention also encompasses the use of the MEKK gene in gene therapy whereby stimulation of differentiation and mitogenesis can be achieved to, for example, alleviate atrophy of certain cell types, such as in Parkinson's disease or Alzheimer's disease by acting as a neurotropic growth factor.

In another embodiment, MEKK is used as a screen for oncogenes and tumor agents by using a screening assay to determine whether such proteins are activated by MEKK. Antibodies made against MEKK can be used to determine the changes in levels of expression of MEKK that might be involved in certain cancers and autoimmune diseases.

The present inventor has recognized that when ligands are bound to B cell or T cell surface receptors, MEKK is a predominant phosphorylated product resulting from the ligation of the receptor. As such MEKK is believed to be a major regulatory protein in the signaling pathway of T and B cells. The regulation of MEKK expression is therefore believed to be useful in the regulation of the growth and differentiation of T and B cells.

MEKK can be used to produce antibodies for use in diagnostic and therapeutic applications. For instance, antibodies against MEKK can be used to screen for tumor cells expressing oncoproteins that are activated by MEKK.

In another embodiment of the invention, the MEKK protein can be used for stimulation of cell growth, mitogenesis and differentiation in vitro. For example, any particular population of cells that one desires to expand and differentiate may be achieved by exposing such cells to effective amounts of MEKK.

In yet another embodiment of the invention, MEKK protein can be provided in a suitable formulation for administration to desired cells to effect an anti-inflammatory response.

In another embodiment of the invention, host cells are transformed with the MEKK gene. The MEKK gene is therefore useful as a tool in gene therapy for the treatment of various diseases, including cancer, autoimmune diseases, neuronal diseases, muscular diseases, allergic responses and inflammatory responses. As used herein, "gene therapy" refers to delivery of a desired gene to a particular cell population to effect expression of that gene in such cell population.

BRIEF DESCRIPTION OF THE DRAWINGS

FIG. 1 (SEQ. ID No: 1) shows the nucleic acid sequence of MEKK and the corresponding amino acid sequence.

DETAILED DESCRIPTION OF THE INVENTION

Figures 2A, 2B:
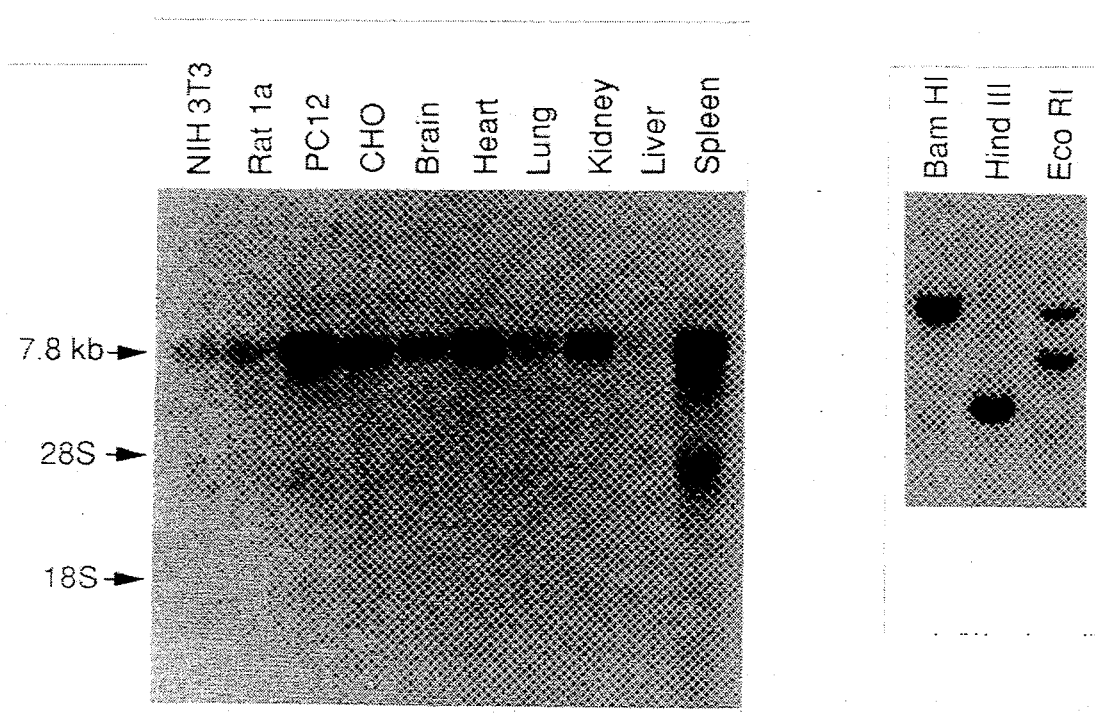
FIG. 2A is a Northern (RNA) blot of a single 7.8 kb MEKK MRNA in several cell lines and mouse tissues.
FIG. 2B shows a Southern (DNA) blot of the MEKK gene.

Ste11 and Byr2 nucleic acid sequences were used to identify mammalian MEK kinase (MEKK) cDNA. Degenerate oligodeoxynucleotides were designed to correspond to regions of sequence identity between the Ste11 and Byr2 genes. With primers and cDNA templates derived from polyadenylated RNA from NIH 3T3 cells, a polymerase chain reaction (PCR) amplification product of 320 base pairs (bp) was isolated and found to be similar in sequence to both Ste11 and Byr2.

This 320 bp cDNA was used as a probe to identify a MEKK cDNA of 3260 bp from a mouse brain cDNA library. The MEKK nucleotide sequence was determined by dedoxynucleotide sequencing of double-stranded DNA. Referring to FIG. 1, (SEQ ID NO: 1) based on the Kozak consensus sequence for initiation codons, the starting methionine can be predicted to occur at nucleotide 486. With this methionine at the start, the cDNA encodes a protein of 672 amino acids, corresponding to a molecular size of 73 kD. There is another in-frame methionine at position 441, which does not follow the Kozak rule, but would yield a protein of 687 amino acid residues (74.6 kD). This size range correlates with the apparent molecular size of 78 to 80 kD of MEKK determined by SDS-polyacrylamide gel electrophoresis (PAGE) and immunoblotting.

The primary sequence of the MEKK protein suggests two functional domains, (i) an $NH_2$-terminal moiety rich in serine and threonine that may serve a regulatory role and (ii) a COOH-terminal protein kinase catalytic domain. Twenty percent of the $NH_2$-terminal 400 amino acids are serine or threonine whereas there are only two tyrosines. Several potential sites of phosphorylation by protein kinase C are apparent in the $NH_2$-terminal region; no Src Homology 2 (SH2 or Src homology 3 (SH3) domains are encoded in the MEKK sequence. The catalytic domain is located in the COOH-terminal half of MEKK.

MEKK is encoded by a 7.8 kb mRNA that is expressed in several cell lines and mouse tissues. FIG. 2A shows a Northern (RNA) blot of a single 7.8-kb MEKK mRNA in several cell lines and mouse tissues. Equal amounts (20 μg) of total RNA were loaded onto the gel as indicated by ethidium bromide staining. Blots were probed with either a 320-bp cDNA fragment encoding a portion of the MEKK kinase domain or an 858-bp fragment encoding a portion of the $NH_2$ terminal region of MEKK. The MEKK mRNA is highly expressed in mouse heart and spleen, whereas low amounts are present in liver. The 7.8 kb MEKK mRNA was identified with probes derived from both the 5' and 3' ends of the MEKK cDNA. Thus, the MEKK cDNA is missing a putative untranslated sequence of about 4 kb.

MEKK is believed to be the product of a single gene. FIG. 2B shows a Southern (DNA) blot of MEKK gene. Mouse genomic DNA (10 μg) was digested with either Bam HI, HIND III, or Eco RI and applied to gels. Blots were probed with a 320-bp fragment of the MEKK gene. The appearance of one band in the BAM HI and HIND III digests suggests that MEKK is encoded by one gene. The appearance of two bands in the ECO RI digest indicates the likely presence of an ECO RI site within an intron sequence spanned by the probe.

Immunoblots of cell lysates probed with affinity-purified antibodies to the 15-amino acid peptide DRPPSRELLKHPVER derived from the COOH-terminus of MEKK defined a prominent band migrating at 78 kD.

Figure 2C:
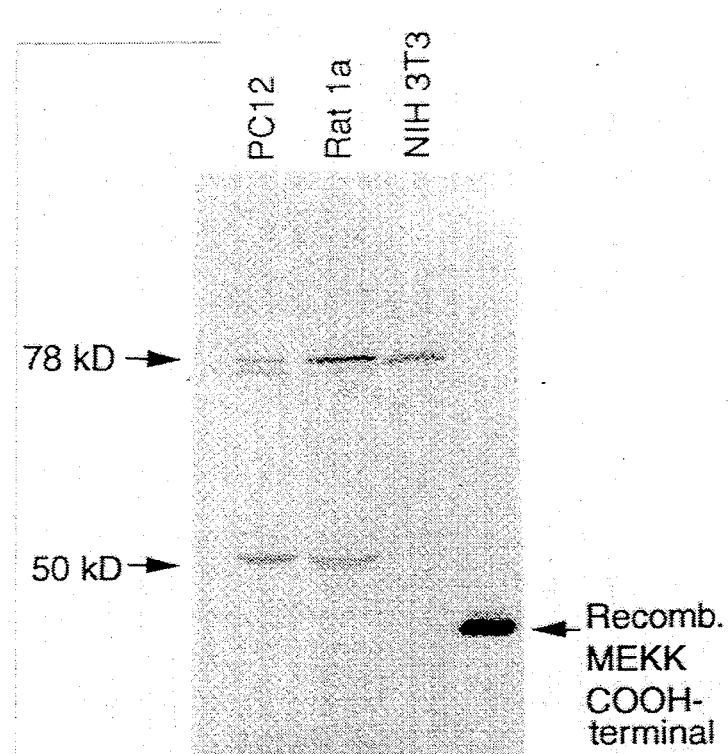
FIG. 2C is an immunoblot showing expression of the 78-kd and 50-kd forms of MEKK in rodent cell lines.

FIG. 2C shows an immunoblot of expression of the 78-kD and 50-kD forms of MEKK in rodent cell lines. Soluble cellular protein (100 μg) or recombinant MEKK COOH-terminal fusion protein (30 ng) was loaded onto the gel for immunoblotting with affinity-purified MEKK antibody (1:300 dilution). Pheochromocytoma (PC12), Rat 1a, and NIH 3T3 cells contained the same 78-kD immunoreactive protein, which often migrated as a doublet on SDS-PAGE. A prominent 50-kD immunoreactive species was also commonly present but varied in intensity from preparation to preparation. It is believed to be a proteolytic fragment of the 78-kD protein. Visualization of both the 78- and 50-kD immunoreactive bands on immunoblots was inhibited by incubation of the 15-amino acid peptide antigen with the antibody. The MEKK protein detected by immunoblotting is similar to the molecular size predicted from the open reading frame of the MEKK cDNA.

Figure 3A:
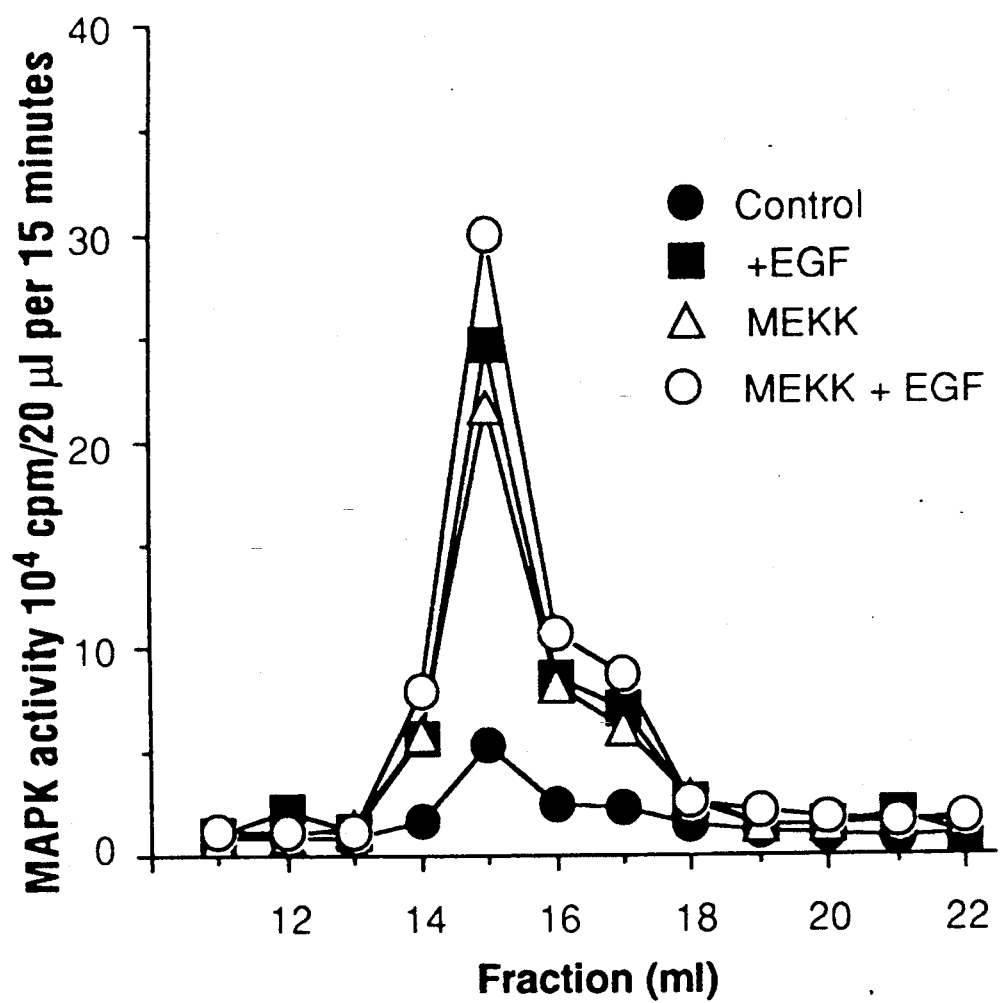
FIG. 3A shows the activation of MAPK in COS cells transfected with MEKK.

The MEKK protein was expressed in COS-1 cells to define its function in regulating the signaling system that includes MAPK. Referring to FIG. 3A, when MEKK was overexpressed in COS-1 cells, MAPK activity was four to five times greater than that in control cells transfected with plasmid lacking a MEKK cDNA insert. COS cells in 100-mm culture dishes were transfected with either the pCVMV5 expression vector alone (1 μg: control) or the pCVMV5 MEKK construct (1 μg: MEKK). After 48 hours, the cells were placed in serum-free medium containing bovine serum albumin (0.1 percent) for 16 to 18 hours to induce quiescence. Cells were then treated with human EGF (30 ng/ml)(+EGF) or buffer (control) for 10 minutes, washed twice in cold phosphate buffered saline (PBS), and lysed in cell lysis buffer containing 50 mM β-glycerophosphate (pH 7.2), 100 μM sodium vanadate, 2 mM MgCl$_2$, 1 mM EGTA Triton X-100 (0.5 percent), leupeptin (2 μg/ml), aprotinin (2μg/ml), and 1 mM dithiothreitol (600 μl). After centrifugation for 10 minutes at maximum speed in a microfuge, COS cell lysates containing 0.5 to 1 mg of soluble protein were subjected to FPLC on a MONO Q column, and eluted fractions were assayed for MAPK activity. The activation of MAPK occurred in COS cells deprived of serum and in the absence of any added growth factor. The activity of MAPK was similar to that observed after stimulation of control cells with EGF. Stimulation of COS cells transiently overexpressing MEKK with EGF resulted in only a slight increase in MAPK activity compared to that observed with MEKK expression alone.

Figure 3B:
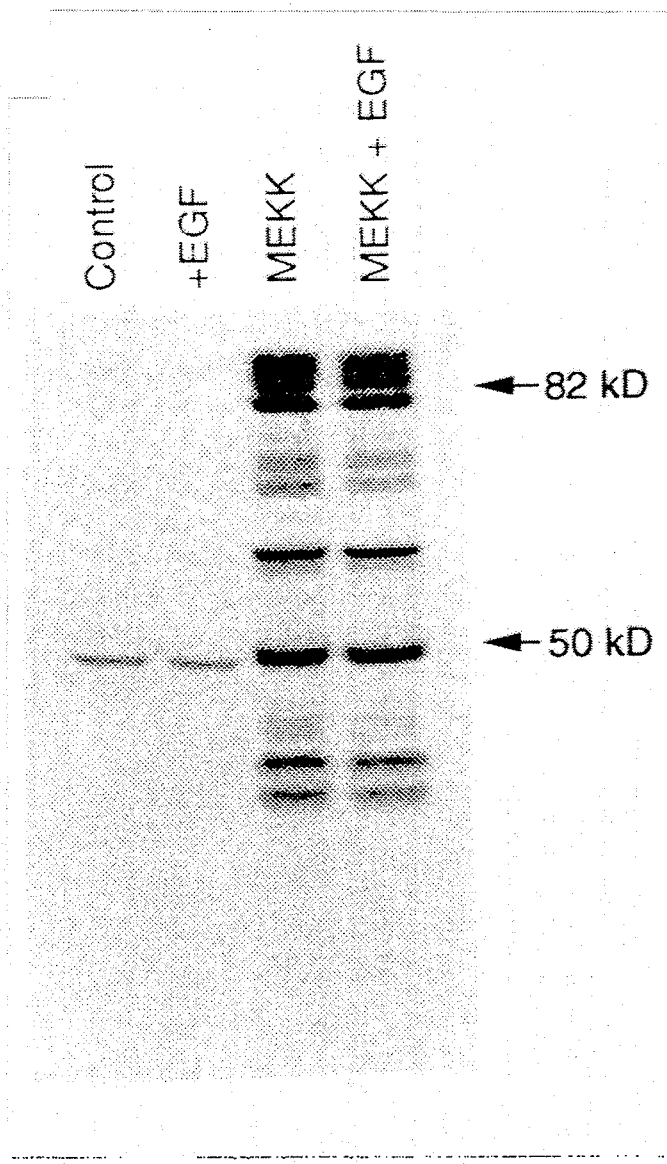
FIG. 3B is an immunoblot showing expression of MEKK in cells transfected with vector only (control) or vector encoding MEKK that were treated with or without EGF.

The MEKK protein was detected in transfected COS cells by immunoblotting. FIG. 3B shows an immunoblot showing expression of MEKK in cells transfected with vector only (control) or vector encoding MEKK that were treated with or without EGF. Equal amounts (100 μg) of soluble protein lysate from COS cells were placed on the gel for immunoblotting. Only the 50-kD MEKK immunoreactive fragment was detected in lysates from control COS cells. Transient expression of MEKK in COS cells yielded a predominant 82-kD band that was slightly larger than that observed in PC12, Rat 1a, or NIH 3T3 cells. This apparently results from the use of a methionine at position 441 rather than 486 for initiation of translation. The bands above the 82-kD MEKK band appear to result from phosphorylation of the MEKK protein. The group of bands below the 82-kD MEKK protein are believed to result from proteolysis. Addition of the 15-amino acid MEKK peptide antigen to the antiserum during immunoblotting prevented detection of all of the immunoreactive bands; these bands were not detected in extracts of control COS cells, an indication that they were derived from the expressed MEKK protein.

Expression of MEKK in COS cells was found to activate MEK, the kinase that phosphorylates and activates MAPK. Recombinant MAPK was used to assay MEK activity in COS cell lysates that had been fractionated by fast protein liquid chromatography (FPLC) on a Mono S column. A cDNA encoding p42 MAPK from *Xenopus laevis* was cloned into the pRSETB expression vector. This construct was used for expression in the LysS strain of *Escherichia coli* BL21(DE3) of a p42 MAPK fusion protein containing a polyhistidine sequence at the NH$_2$-terminus. Cultures containing the expression plasmid were grown at 37° C. to an optical density of 0.7 to 0.9 at 600 nM. Isopropyl-β-thiogalactopyranoside (0.5 mM) was added to induce fusion protein synthesis and the cultures were incubated for 3 hours. The cells were then collected and lysed by freezing, thawing, and sonication. The lysate was centrifuged at 10,000 g for 15 minutes at 4° C. The supernatant was then passed over a Ni2+ − charged Sepharose resin and the soluble recombinant MAPK was eluted in sodium phosphate buffer (pH 4.5). The purified recombinant MAPK was more than 80 percent pure. The purified recombinant MAPK served as a substrate for MEK and catalyzed the phosphorylation of a peptide consisting of residues 662 to 681 of the EGF receptor (EGFR$^{662-681}$).

Figure 4A:
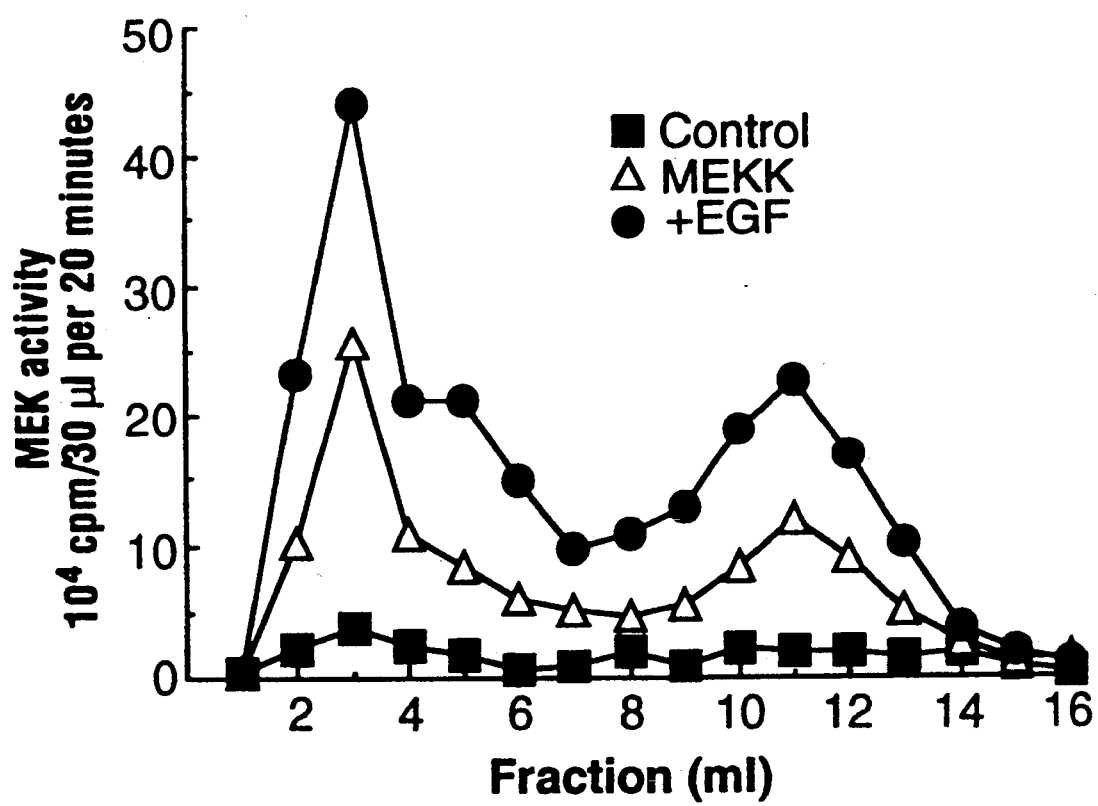
FIG. 4A shows the activation and phosphorylation of MEK in COS cells transfected with MEKK.

Soluble cell lysates from COS cells transiently transfected with MEKK, mock-transfected (control), or mock-transfected and treated with EGF (30 ng/ml) (+EGF), were fractionated by FPLC on a Mono S column and endogenous MEK activity was measured. Endogenous MAPK eluted in fractions 2 to 4, whereas MEK was contained in fractions 9 to 13. For assaying endogenous MEK activity, cells were washed twice in cold PBS and lysed in 650 μl of a solution containing 50 mM β-glycerophosphate, 10 mM 2-N-morpholinoethane-sulfonic acid (pH 6.0), 100 μM sodium vanadate, 2 mM MgCl$_2$, 1 mM EGTA, Triton X-100 (0.5 percent), leupeptin (5 μg/ml), aprotinin (2 μg/ml), and 1 mM dithiothreitol. After centrifugation at maximum speed for 10 minutes in a microfuge, soluble cell lysates (1 to 2 mg of protein) were applied to a Mono S column equilibrated in elution buffer (50 mM β-glycerophosphate, 10 mM MES (pH 6.0), 100 μM sodium vanadate, 2 mM MgCl$_2$, 1 mM EGTA, and 1 mM dithiothreitol). The column was washed with buffer (2 ml) and bound proteins were eluted with a 30-ml linear gradient of 0 to 350 mM NaCl in elution buffer. A portion (30 μl) of each fraction was assayed for MEK activity by mixing with buffer (25 mM β-glycerophosphate, 40 mM N-(2-hydroxyethyl) ethanolsulfonic acid) (pH 7.2) 50 mM sodium vanadate, 10 mMMgCl$_2$, 100 μM γ-$^{32}$P-ATP (3000 to 4000 cpm/pmol), inhibitor protein-20 (IP-20; TTYADFIASGRTGRRNAIHD; 25 μg/ml), 0.5 mM EGTA, recombinant MAP kinase (7.5 μg/ml), and 200 μM EGFR$^{653-681}$) in a final volume of 40 μl. After incubation at 30° C. for 20 minutes, the incorporation of γ-$^{32}$P-ATP into EGFR$^{652-681}$ was measured. In this assay, the ability of each column fraction to activate added recombinant MAPK was measured by the incorporation of γ-$^{32}$P-ATP into the MAPK substrate, a peptide derived from the EGF receptor (EGFR). Referring to FIG. 4A, the first peak of activity eluted represents endogenous activated MAPK, which directly phosphorylates the EGFR peptide substrate.

Figure 4B:
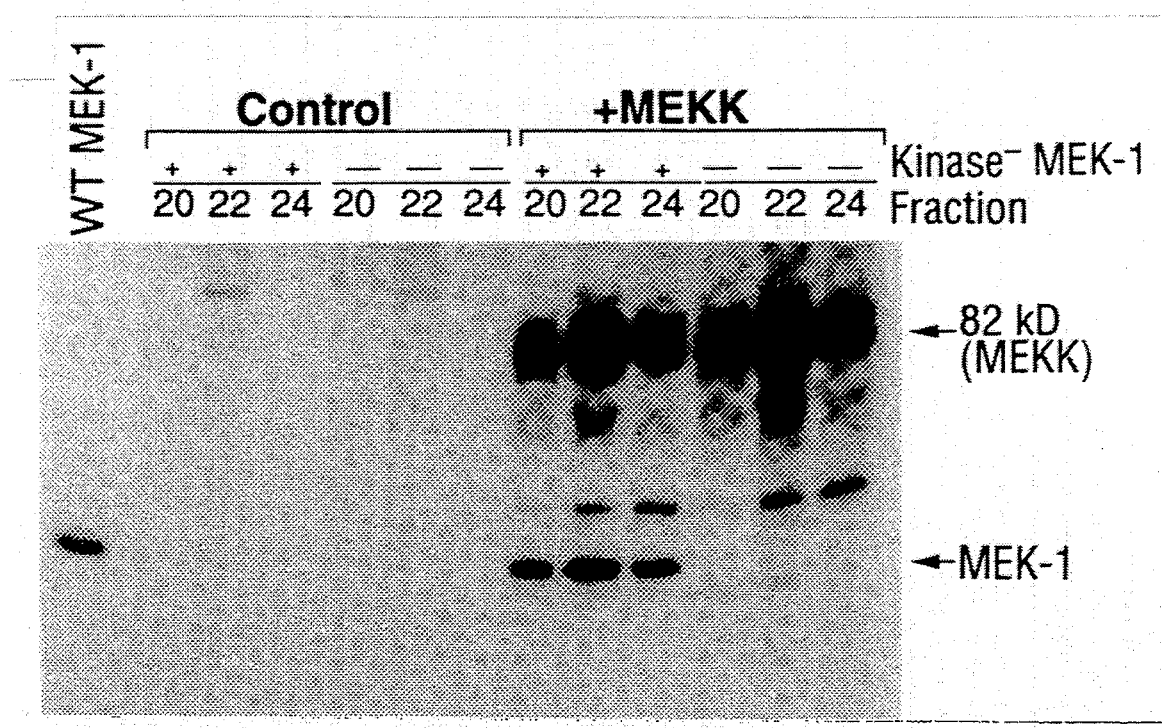
FIG. 4B shows the phosphorylation of MEK-1 by MEKK.

The second peak of activity represents the endogenous MEK in COS cells. Endogenous MEK activity was characterized by fractionation of Mono S FPLC. FIG. 4B indicates that endogenous MEK was activated in cells overexpressing MEKK; the activity of MEK was approximately half of that observed in control cells stimulated with EGF. Thus, expression of MEKK appears to activate MAPK by activating MEK.

COS cell lysates were fractionated by FPLC on a Mono Q column to partially purify the expressed MEKK. Purified recombinant MEK-1 was then used as a substrate for MEKK in the presence of $\gamma$-$^{32}$P-ATP to determine whether MEKK directly phosphorylates MEK-1. A cDNA encoding MEK-1 was obtained from mouse B cell cDNA templates with the polymerase chain reaction and oligodeoxynucleotide primers corresponding to portions of the 5' coding region and 3' untranslated region of MEK-1. The catalytically inactive MEK-1 was generated by site-directed mutagenesis of Lys$^{343}$ to Met. The wild-type MEK-1 and catalytically inactive MEK-1 proteins were expressed in pRSETA as recombinant fusion proteins containing a polyhistidine sequence at their NH$_2$-termini.

Figure 4C:
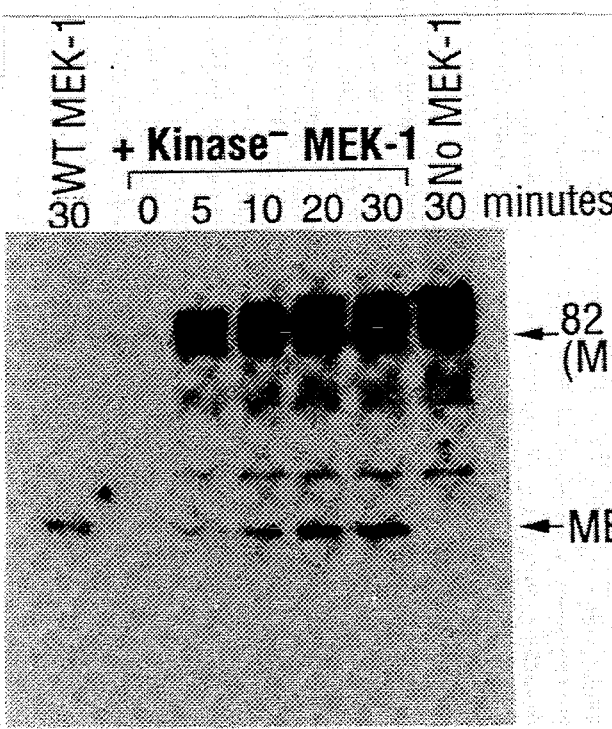
FIG. 4C shows the time course of phosphorylation of MEK-1 by MEKK expressed in COS cells.
Figure 4D:
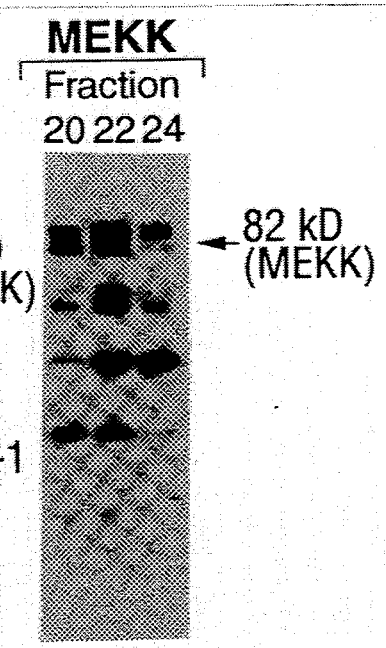
FIG. 4D is an immunoblot of MEKK overexpressed in COS cells.

Lysates from COS cells transfected with MEKK or mock-transfected (control) were subjected to FPLC on a Mono Q column as described above. Portions (20 $\mu$l) of fractions containing MEKK were mixed with buffer containing (50 mM $\beta$-glycerophosphate (pH 7.2), 100 $\mu$M sodium vanadate, 2 (mM MgCl$_2$, 1 mM EGTA, 50 $\mu$M ATP, IP-20 (50 $\mu$g/ml), and 10 $\mu$l $\gamma$-$^{32}$-P-ATP in a reaction volume of 40 $\mu$l and incubated for 40 minutes in the presence (+) or absence (−) of recombinant, catalytically inactive MEK-1 (150 ng)(kinase-MEK-1). Reactions were stopped by the addition of 5×SDS sample buffer (10 $\mu$l), 1×SDS buffer contains 2 percent SDS, 5 percent glycerol, 62.5 mM tris-HCl (pH 6.8), 5 percent $\beta$-mercaptoethanol, and 0.001 percent bromophenol blue. The samples were boiled for 3 minutes and subjected to SDS-PAGE and autoradiography. Autophosphorylated recombinant wild-type MEK-1 (WT MEK-1) comigrated with phosphorylated catalytically inactive MEK-1. MEKK was capable of phosphorylating MEK-1. Corresponding fractions of lysates from control cells, however, were not able to phosphorylate MEK-1. A modified form of MEK-1 that is catalytically inactive was used in the phosphorylation assay to ensure that it did not autophosphorylate as does wild-type MEK-1. Phosphorylation of catalytically inactive MEK-1 by MEKK was time dependent (FIG. 4C); MEKK was also phosphorylated. Fraction 22 from FPLC on a Mono Q column (20 $\mu$l) was incubated with or without recombinant catalytically inactive MEK-1 (0.15 $\mu$g) for the indicated times. Phosphorylation of Kinase MEK-1 and MEKK was visable after 5 minutes and maximal after about 20 minutes. The time-dependent increase in MEKK phosphorylation correlated with a decreased mobility of the MEKK protein during SDS-PAGE. Immunoblotting demonstrated that the MEKK protein co-eluted (after FPLC on a Mono Q column) with the peak of activity (fraction 22) that phosphorylated MEK (FIG. 4D). The slowly migrating species of MEKK were also detected by immunoblotting.

Figure 5A:
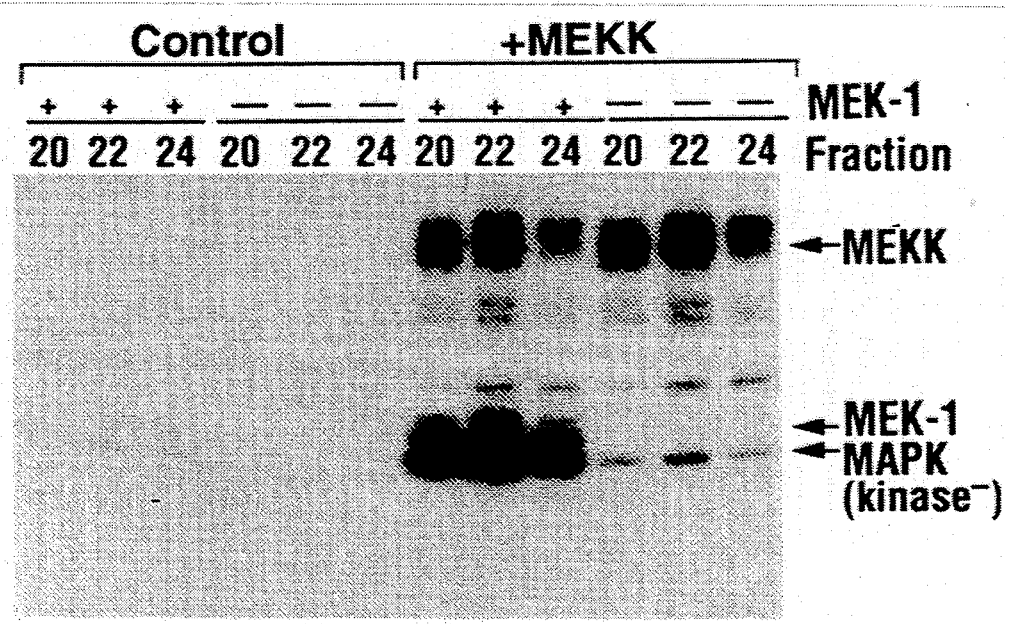
FIG. 5A shows the phosphorylation of MAPK by activated MEK-1.

To determine whether the phosphorylation of MEK by overexpressed MEKK resulted in activation of MEK, recombinant wild-type MEK-1 and a modified form of MAPK that is catalytically inactive were used in a coupled assay system. COS cell lysates were separated by Mono Q-FPLC and fractions containing MEKK were assayed for their ability to activate added wild-type MEK-1 such that it would phosphorylate catalytically inactive recombinant MAPK in the presence of $\gamma$-$^{32}$P-ATP. Lysates from COS cells transfected with MEKK or mock-transfected (control) were fractionated by FPLC on a Mono Q column and portions (20 $\mu$l) of fractions containing MEKK were mixed with buffer. Each fraction was incubated in the presence (+) or absence (−) of purified recombinant wild-type MEK-1 (150 ng) and in the presence of purified recombinant, catalytically inactive (kinase$^-$) MAPK (300 ng). Referring to FIG. 5A, fractions 20 to 24 from lysates of COS cells transfected with MEKK activated MEK-1. Thus, MEKK phosphorylated and activated MEK-1, leading to MAPK phosphorylation.

Figure 5B:
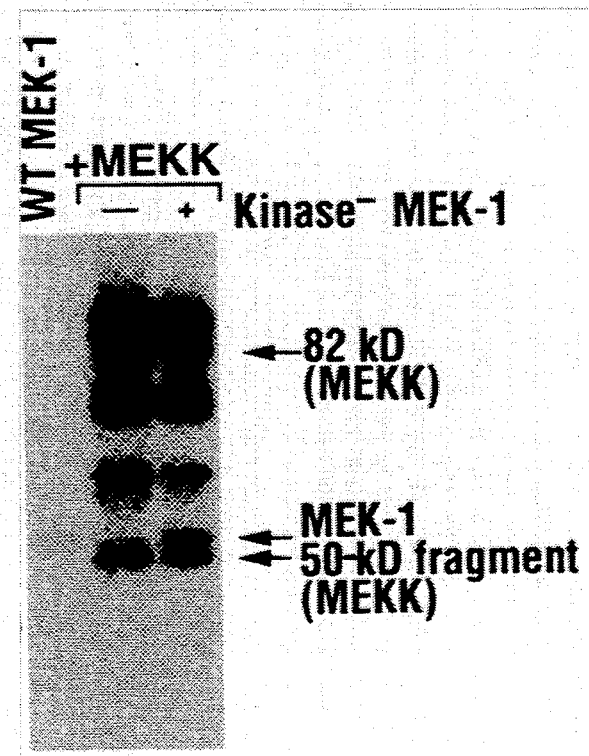
FIG. 5B shows phosphorylation of MEK-1 by immunoprecipitated MEKK.

To insure that MEKK activated MEK directly, and not through the activation of one or more other kinases contained in the column fractions, overexpressed MEKK was immunoprecipitated from COS cell lysates with an antiserum to COOH-terminal MEKK fusion protein. The MEKK cDNA was digested with Pst I and Kpn 1, thereby creating a 1670-bp fragment that encodes the catalytic domain of MEKK. This fragment was expressed in pRSETC as a recombinant fusion protein containing a polyhistidine sequence at its NH$_2$-terminus. The purified COOH-terminal MEKK fusion protein was used to generate polyclonal antisera. Immunoprecipitated MEKK was resuspended in 10 to 15 $\mu$l of PAN (10 mM piperazine, N'-bis-2-ethanesulfonic acid (Pipes) (pH 7.0), 100 mM NaCl, and aprotinin (20 $\mu$g/ml) and incubated with (+) or without (−) catalytically inactive MEK-1 (150 ng) and 25 $\mu$Ci of $\gamma$-$^{32}$-P-ATP in 20 mM pipes (pH 7.0) 10 mMMnCl$_2$, and aprotinin (20 $\mu$g/ml) in a final volume of 20 $\mu$l for 15 minutes 30° C. Reactions were stopped by the addition of 5×SDS sample buffer (5 $\mu$l). The samples were boiled for 3 minutes and subjected to SDS-PAGE and autoradiography. Referring to FIG. 5B, MEKK phosphorylated catalytically inactive MEK-1, which comigrated with wild-type MEK-1 on SDS-PAGE. Several phosphorylated bands of overexpressed MEKK were detected in the immunoprecipitates. These bands probably resulted from autophosphorylation of MEKK and corresponded to the forms of MEKK identified by immunoblotting of lysates from COS cells transfected with MEKK (FIG. 2C). Immunoprecipitates obtained with pre-immune serum contained no MEKK and did not phosphorylate MEK-1. Thus, MEKK appears to directly phosphorylate MEK, although an associated kinase that coimmunoprecipitates which MEKK cannot be unequivocally excluded.

Figure 6A:
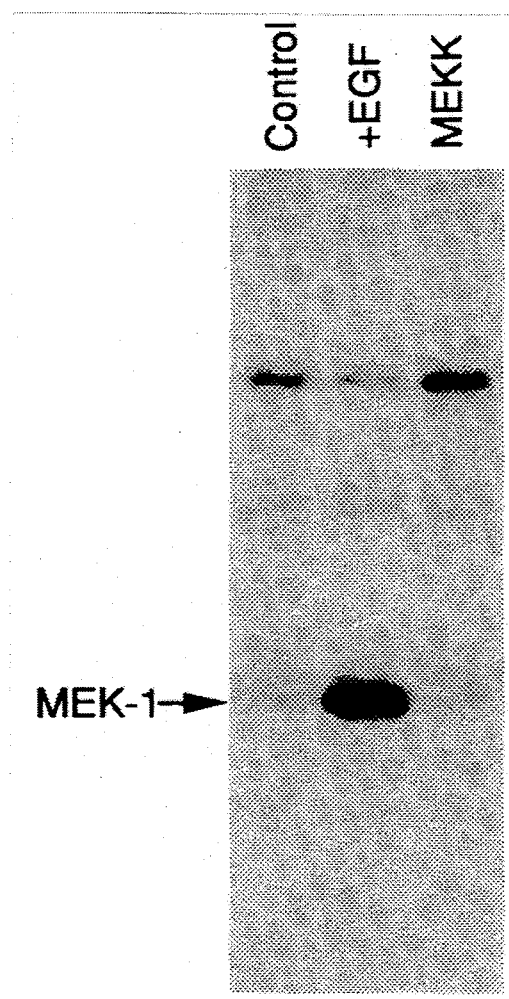
FIG. 6A shows the phosphorylation of MEK-1 by activated Raf.
Figure 6B:
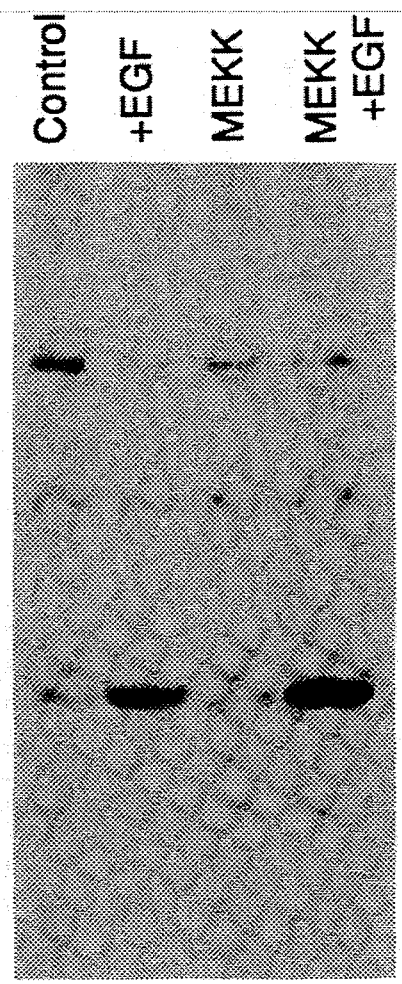
FIG. 6B shows the activity of Raf in COS cells overexpressing MEKK treated with EGF.
Figure 7:
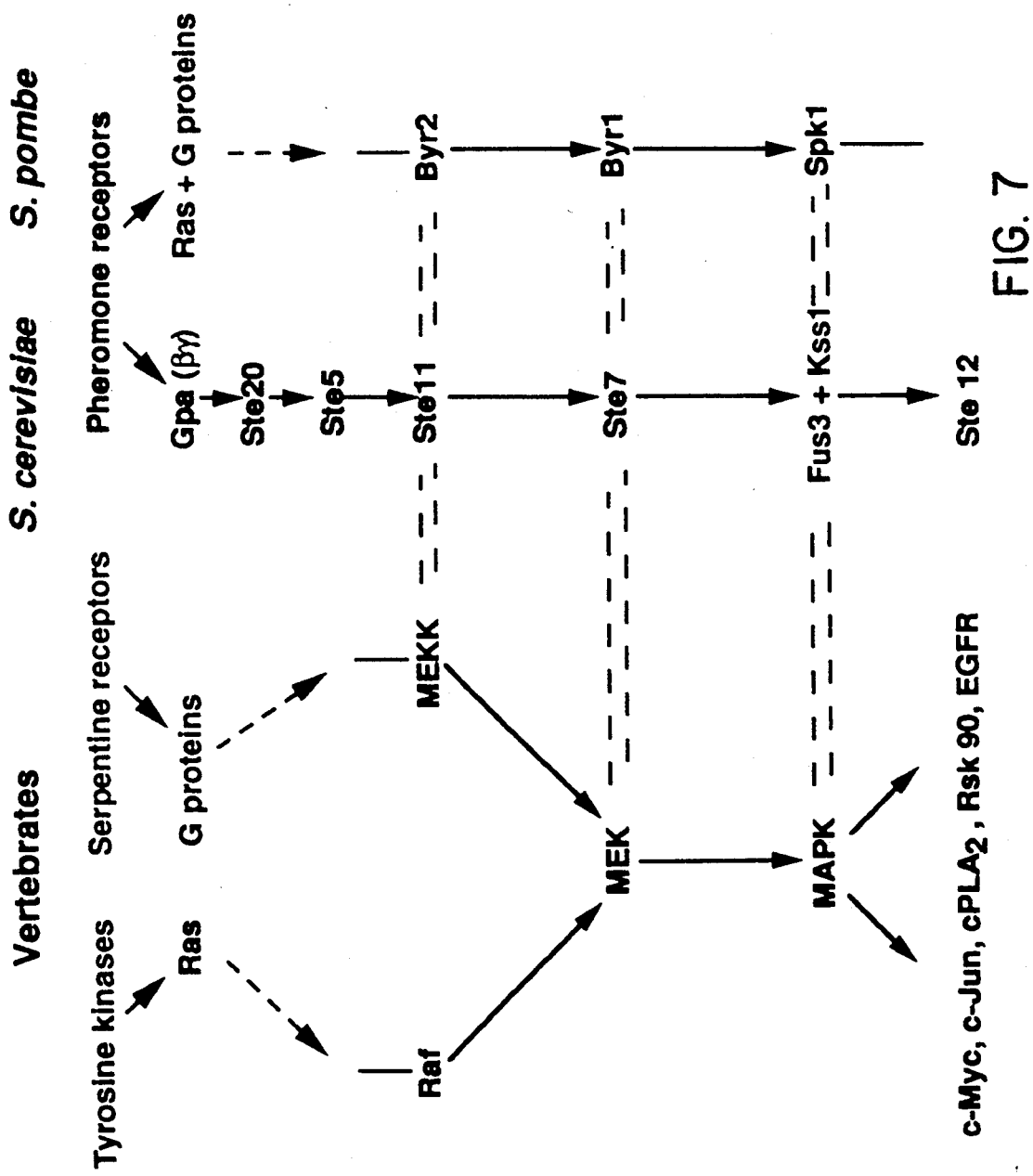
FIG. 7 is a schematic representation of the signal pathways of vertebrates and yeast.

The results show that MEKK can phosphorylate and activate MEK, which in turn phosphorylates and activates MAPK. Raf can also phosphorylate and activate MEK (FIG. 6). COS cells deprived of serum were stimulated with EGF, and Raf was immunoprecipitated with an antibody to the COOH-terminus of Raf-1. Cos cells were transiently transfected with vector alone (control) or with the PCV/M5-MEKK construct (MEKK). Quiescent control cells were treated with or without human EGF (30 ng/ml) for 10 minutes and Raf was immunoprecipitated from cell lysates with an antibody to a COOH-terminal peptide from Raf. Immunoprecipitated Raf was incubated with catalytically inactive MEK-1 (150 ng) and 25 $\mu$l of $\gamma$-$^{32}$P-ATP. The immunoprecipitated Raf phosphorylated MEK-1 in the presence of $\gamma$-$^{32}$P-ATP (FIG. 6A). Little or no phosphorylation of MEK-1 by Raf was observed in immunoprecipitates of Raf from COS cells overexpressing MEKK. Treatment of COS cells overexpressing MEKK with EGF resulted in a similar degree of phosphorylation of MEK-1 by immunoprecipitated Raf (FIG. 6B). Cells transfected with MEKK and deprived of serum were treated with EGF, and Raf was immunoprecipitated and incubated with catalytically inactive MEK-1. Equal amounts of Raf were immunoprecipitated in each sample as demonstrated by immunoblotting with antibodies to Raf. The slowest migrating band represents an immunoprecipitated phosphoprotein that is unrelated to Raf or MEK-1. The amount of Raf in the immunoprecipitates from control cells and cells transfected with MEKK was similar as shown by subsequent SDS-PAGE and immunoblotting with the antibody to Raf. Thus, both MEKK and Raf can independently activate MEK.

Identification of the MEKK from mouse further substantiates the conservation in regulation of the MAPK system between yeast and mammals. The results indicate that the mammalian regulatory network controlling MAPK is more complicated than that in yeast. Both MEKK and Raf activate MEK, a convergence point immediately upstream of MAPK for various signals from the cell surface. Raf regulates the MAPK network primarily in response to receptors that have associated tyrosine kinase activity, whereas MEKK might mediate primarily signals originating from receptors that activate G proteins and protein kinase C. This possibility is supported by the findings in specific cell types that down regulation of protein kinase C does not inhibit activation of MAPK in response to growth factors, but does inhibit activation of MAPK in response to agents that stimulate the muscarinic $M_1$ receptor. The demonstration that Ste20, a protein kinase in *S. cerevisiae*, is upstream of Ste11 in the pheromone-response pathway further supports this hypothesis. In PC12 cells, re-expression of dominant negative mutant Ras does not inhibit activation of MAPK in response to stimulation of G protein-coupled receptors or activation of protein kinase C, but does inhibit activation of MAPK in response to neuronal growth factor (NGF) or fibroblast growth factor (FGF). It is believed, however, that more complex, cell type specific roles of Raf and MEKK in integrating tyrosine kinase and G protein-couple signaling exist. Defining MEKK and Raf as a divergence in the MAPK network provides a mechanism for differential regulation of this system. To determine if a similar or distinct MEK activity is involved in activation of MAPK though $G_i$ protein coupled receptors, the present investigator investigated MEK activity in cell lysates from thrombin stimulated Rat 1a cells. Thrombin stimulated cells exhibited a MEK activity which co-fractionated with the major MEK peak detected in EGF stimulated cells. The magnitude of MEK activity from thrombin challenged cells was generally two to three-fold less than that observed with EGF stimulation, which correlates with the smaller MAPK response the present inventor has observed in thrombin challenged cells.

Differential regulation of MEK in Rat 1a and NIH3T3 cells expressing gip2, v-src, v-ras, or v-raf led the present inventor to investigate the protein kinases that are putative regulators of MEK-1. Recently,, it was shown that Raf-1 can phosphorylate and activate MEK. Raf activation was assayed in the following manner. Cells were serum starved and challenged in the presence or absence of growth factors, as described above. Serum starved Rat 1a cells were challenged with buffer alone or with EGF and Raf was immunoprecipitated using an antibody recognizing the C terminus of Raf. Cells were lysed by scraping in ice cold RIP buffer (50 mM Tris, pH 7.2, 150 mM NaCl, 0.1% SDS, 0.5% sodium deoxycholate, 1.0% Triton X 100, 10 mM sodium pyrophosphate, 25 mM sodium glycerophosphate, 2 mM sodium vanadate, 2.1 µg/ml aprotinin) and were microfuged for 10 minutes to remove nuclei. The supernatants were normalized for protein content and precleared with protein A Sepharose prior to immunoprecipitation with rabbit antiserum to the C terminus of Raf-1 and protein A Sepharose for 2–3 h at 4° C. The beads were washed twice with ice cold RIPA and twice with PAN (10 mM Pipes, pH 7.0, 100 mM NaCl, 21 µg/ml aprotinin). A portion of the immunoprecipitate was diluted with SDS sample buffer and used for immunoblot analysis. The remainder was resuspended in kinase buffer (20 mM Pipes pH 7.0, 10 mM $MnCl_2$, 150 ng kinase-inactive MEK-1, 30 µCi $\gamma$-$^{32}$P-ATP and 20 µg/ml aprotinin) in a final volume of 50 µl for 30 rain at 30° C. Wild type recombinant MEK-1 was autophosphorylated in parallel as a marker. Reactions were terminated by the addition of 12.5 µl 5X SDS sample buffer, boiled for 5 min and subjected to SDS-PAGE and autoradiography.

The immunoprecipitated Raf, in the presence of $\gamma$-$^{32}$P-ATP, was able to phosphorylate MEK-1. The recombinant MEK-1 used in this assay was kinase inactive to ensure it did not autophosphorylate as is observed with wild type MEK-1. Little or no phosphorylation of MEK-1 by Raf was observed in immunoprecipitates from control cells. EGF challenge clearly stimulated Raf catalyzed phosphorylation of MEK-1; in contrast, thrombin challenge of Rat 1a cells did not measurably activate Raf even though endogenous MEK was clearly activated. EGF stimulated Raf phosphorylation of recombinant MEK-1 by approximately 2.6-fold over basal. Little phosphorylation of MEK by Raf was observed in Raf immunoprecipitates from Gip2 or v-Src expressing Rat 1a cells. EGF stimulation was still capable of activating Raf catalyzed phosphorylation of MEK-1 in these cell lines by 1.8 and 1.4-fold, respectively. The blunting of the EGF response in Gip2 and v-Src expressing cells is likely a result of desensitization of the EGF receptor upon constitutive activation of MAPK. The amount of Raf in the immunoprecipitates was shown to be similar by subsequent SDS-PAGE and immunoblotting using Raf antibody. Since thrombin stimulation of MEK is two to three-fold over basal, at least a 1.5-fold stimulation of MEK phosphorylation is expected if Raf significantly contributed to MEK activation by this growth factor. This level of activation was detectable in the EGF stimulated Gip2 and v-Src expressing cells lines. Thus, it is unlikely that the failure to detect thrombin activation of Raf is due to the sensitivity of the assay. Thrombin stimulation of MAPK is maximal at 3 minutes. Stimulation of Rat 1a cells for 1 or 5 minutes with thrombin did not increase Raf activity.

In NIH3T3 cells, as in Rat 1a cells, Egf activates Raf approximately 2.7-fold, while thrombin does not. V-Raf expressing NIH3T3 cells showed no increase in MEK-1 phosphorylation. This result was unexpected since MEK was clearly activated in v-Raf expressing NIH3T3 cells. Both the p90 and p75 gag-raf fusion proteins in addition to c-Raf-1 were immunoprecipitated from v-Raf NIH3T3 cells by the antisera. P75gag-raf has been shown to exhibit protein kinase activity, but it is possible that the $NH_2$ terminal gag fusion protein sterically hinders Raf phosphorylation of recombinant MEK-1 in the in vitro assay system. Further studies will have to be done to measure v-Raf kinase activity. The results argue that activation of MEK cannot be accounted for exclusively by the activation of Raf. Additional regulatory kinases for MEK must exist which contribute to MEK activation in thrombin stimulated, $G_i$ protein coupled pathways and in gip2 and v-src transfected cells.

MAPKs are serine/threonine kinases that are thought to be key intermediate molecules in various signal transduction pathways. MAPKs are in turn phosphorylated and activated by MEKs.

Constitutive activation of MEK accounts for most if not all of the increased MAPK activity in oncogene transfected cells. Gip2 and v-Src activated MEK in Rat 1a cells, while v-Raf most effectively activated MEK in NIH3T3 cells. These oncoproteins activated a similar MEK activity as growth factors. No significant level of MEK stimulation in v-Ras transfected NIH3T3 cells was detected. The findings indicate for a rather tight linkage between MAPK and MEK activation. The present inventor has have not observed a significant activation of MAPK independent of MEK activation in oncoprotein expressing growth factor-stimulated cells.

The sensitivity of Raf activation assays involving phosphorylation of kinase inactive MEK-1 suggests that one should be able to easily detect a Raf activity that is 20–25% of that observed with EGF stimulation of both Rat 1a and NIH3T3 cells. Failure to detect Raf activation in response to thrombin, where both MEK and MAPK activity are easily detected, suggests Raf is not significantly activated by thrombin in Rat 1a and NIH3T3 cells. This finding suggests an additional protein kinase other than Raf is capable of phosphorylating and activating MEK-1. The present inventor has recently cloned and expressed a mouse MEK kinase (MEKK) that is unrelated to and independent of Raf. Both MEKK and Raf were shown to phosphorylate and activate MEK-1. MEKK is the mouse homolog of the yeast protein kinases Ste 11 and Byr2; MEK is the mouse homolog of the yeast protein kinases Ste7 and Byr1. Raf is unrelated in sequence to Ste11 and Byr2, suggesting that Raf represents a divergence in mammalian cells from the pheromone responsive protein kinase system defined in yeast.

Experiments indicate that Raf and MEKK both activate MEK, which functions as a convergence point for multiple protein kinases that are involved in MAPK activation. Thus, Raf and MEKK are protein kinases at the divergence for signal inputs initiated by different cell surface receptors. It is believed that MEKK is a thrombin regulated kinase that regulates MEK in Rat 1a and NIH3T3 cells. It is also believed that Raf and MEKK are differentially regulated by oncoproteins.

The placement of MEK between MAPK and upstream regulators of MAPK provides integration but also independence of signal networks initiated by growth factor receptors. For example, the serine/threonine kinases Raf and MEKK can phosphorylate MEK, but most likely phosphorylate other proteins as well. MEK is a specialized dual tyrosine/threonine kinase for the selective regulation of MAPK.

One aspect of the present invention relates to the recognition that MEKK activates MAPK. For instance, MAPK is known to be involved in various cellular pathways in mammalian systems. MAPK is known to be involved in cellular mitogenesis, DNA synthesis, cell division and differentiation. MAPK is also recognized as being involved in the activation of oncogenes, such as c-Jun and c-Myc. While not bound by theory, the present inventor believes that MAPK is also intimately involved in various abnormalities having a genetic origin. MAPK is known to cross the nuclear membrane and is believed to be at least partially responsible for regulating the expression of various genes. As such, MAPK is believed to play a significant role in the instigation or progression of cancer, neuronal diseases, autoimmune diseases, allergic reactions, wound healing and inflammatory responses. The present inventor, by being first to identify nucleic acid sequences encoding MEKK, recognized that it is now possible to regulate the expression of MEKK, and thus regulate the activation of MAPK.

It is also known that MEKK functions in various other capacities besides the activation of MAPK. As such, it is within the scope of the present invention to regulate the expression of MEKK to effect the regulation of other cellular activities that are regulated, either by stimulation or inhibition, by MEKK.

Another aspect of the present invention relates to the recognition that both MEKK as well as Raf are able to activate MAPK. The present inventor has discovered that while MEKK is structurally distinct from Raf, both Raf and MEKK are involved in the regulation of MAPK activity. Therefore, it is within the scope of the present invention to either stimulate or inhibit the expression of Raf and MEKK to achieve desired regulatory results. Thus, in one embodiment, MEKK expression can be inhibited, for example, by use of antisense nucleic acid sequences, in order to block MEKK activity. Alternatively, the expression of Raf can be similarly regulated in the same cell to achieve maximum inhibition of MAPK activity. Regulation of the MAPK system can therefore be fine-tuned by inhibition and/or stimulation of either or both Raf and MEKK expression.

It is within the scope of the present invention to regulate the expression of MEKK through the use of well-known recombinant DNA expression techniques. For example, suitable host cells can be transformed with the MEKK sequence and suitable control elements can be operatively linked with the MEKK sequence to achieve desired expression.

The amount of MEKK enzyme present in the cell can be increased in a variety of ways including, but not limited to, substantially derepressing synthesis of the enzyme, amplifying the copy number of a nucleic acid sequence encoding the enzyme, and combinations thereof.

As used herein, "substantially derepressing synthesis of the enzyme" refers to production of greater amounts of the enzyme than are normally produced by wild-type cells such that the amount and/or rate of substrate-to-product conversion is higher than in wild-type cells (i.e., there is enhanced conversion of substrate to product). Derepression of MEKK enzyme synthesis can be accomplished in a variety of ways, including interfering with the regulatory controls normally exerted over transcription and/or translation of the gene encoding the enzyme and increasing the stability of the messenger RNA (mRNA) corresponding to the enzyme. For example, synthesis of an enzyme which is normally subject to repression, may be increased by at least partially inactivating the respective repressor and/or modifying the operator sequence to reduce the ability of the repressor to bind to it. Modification of transcription (e.g., promoter) and/or translation (e.g., Shine Delgarno sequence) control signals (e.g., initiation, elongation, and/or termination signals) can also enhance both the rate and amount of enzyme production. Methods to derepress enzyme synthesis include recombinant DNA techniques.

As used herein, amplifying the copy number of a nucleic acid sequence in a cell can be accomplished either by increasing the copy number of the nucleic acid sequence in the cell's genome or by introducing additional copies of the nucleic acid sequence into the cell by transformation. Copy number amplification is conducted in a manner such that greater amounts of enzyme are produced, leading to enhanced conversion of substrate to product. For example, recombinant molecules containing nucleic acids of the present invention can be transformed into cells to enhance enzyme synthesis. Transformation can be accomplished using any process by which nucleic acid sequences are inserted into a cell. Transformation techniques include, but are not limited to, transfection, electroporation, microinjection, lipofection, adsorption, and protoplast fusion. After transformation, the cell can produce multiple copies of the nucleic acid sequence, which can either remain on extrachromosomal vectors or be integrated into the host genome. Prior to transformation, the nucleic acid sequence on the recombinant molecule can be manipulated to encode an enzyme having a higher specific activity.

A functionally equivalent enzyme can, but need not, share significant amino acid sequence homology with the given enzyme. A functionally equivalent enzyme can be a modified version of the given enzyme in which amino acids have been deleted (e.g., a truncated version of the enzyme), inserted, inverted, substituted and/or derivatized (e.g., glycosylated, phosphorylated, acetylated) such that the modified enzyme has a biological function substantially similar to that of the given enzyme. Modifications can be accomplished by techniques known in the art including, but not limited to, direct modifications to the protein or modifications to the gene encoding the protein using, for example, classic or recombinant DNA techniques to effect random or targeted mutagenesis. Functionally equivalent enzymes can be selected using assays set up to measure enzyme activity.

It is within the scope of the present invention to use a variety of methods, such as those described above, to deregulate the MEKK enzyme. A preferred method to obtain a cell containing a deregulated enzyme is to transform the cell with a MEKK nucleic acid sequence encoding the enzyme or with a MEKK functionally equivalent nucleic acid sequence. As used herein, a "functional equivalent" of a particular nucleic acid sequence is a nucleic acid sequence that encodes a protein having substantially the same biological function as the protein encoded by the particular gene.

Functionally equivalent nucleic acid sequences can include nucleic acid sequences containing modifications, such as nucleotide deletions, additions, inversions, and/or substitutions that do not substantially interfere with the nucleic acid sequence's ability to encode a biologically active enzyme. That is, functionally equivalent nucleic acid sequences of the present invention encode enzymes having a biological activity similar to their natural counterparts. Functionally equivalent eukaryotic nucleic acid sequences can also include intervening and/or untranslated sequences surrounding and/or within the coding regions of the nucleic acid sequences.

A functionally equivalent nucleic acid sequence can be obtained using methods known to those skilled in the art (see, for example, Sambrook et al., Molecular Cloning: A Laboratory Manual, Cold Spring Harbor Labs Press, 1989, which is incorporated herein by reference in its entirety.). For example, nucleic acid sequences can be modified using a variety of techniques including, but not limited to, classic mutagenesis techniques and recombinant DNA techniques, such as site-directed mutagenesis, chemical treatment of a nucleic acid to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid sequences, and combinations thereof. Functionally equivalent nucleic acids can be selected from a mixture of modified nucleic acid sequences by screening for the function of the protein encoded by the nucleic acid sequence. A number of screening techniques are known to those skilled in the art including, but not limited to, complementation assays, binding assays, and enzyme assays.

Transformation can be accomplished using any process by which nucleic acid sequences are inserted into a cell. Transformation techniques include, but are not limited to, transfection, electroporation, microinjection, lipofection, adsorption, and protoplast fusion. A recombinant cell may remain unicellular or may grow into a tissue or a multicellular organism. Transformed nucleic acid sequences of the present invention can remain extrachromosomal or can integrate into one or more sites within a chromosome of a host cell in such a manner that their ability to be expressed is retained. Integrated nucleic acid sequences often are more stable than extrachromosomal sequences. As such, it is within the scope of the present invention that expression of nucleic acid sequences encoding the enzymes of the present invention may be due to expression of plasmid sequences or to sequences integrated into the host genome.

Preferably, a recombinant cell is produced by transforming a host cell with one or more recombinant molecules, each containing one or more nucleic acid sequences of the present invention operatively linked to an expression vector containing one or more transcription control sequences. A cell can be transformed with one or more recombinant molecules.

As used herein, the phrase "operatively linked" refers to insertion of a nucleic acid sequence into an expression vector in a manner such that the sequence is able to be expressed when transformed into a host cell. As used herein, an expression vector is a DNA or RNA vector that is capable of transforming a host cell, of replicating within the host cell, and of effecting expression of a specified nucleic acid sequence. Expression vectors can be either prokaryotic or eukaryotic, and are typically viruses or plasmids.

Nucleic acid sequences of the present invention can be operatively linked to expression vectors containing regulatory sequences such as promoters, operators, repressors, enhancers, termination sequences, origins of replication, and other regulatory sequences that are compatible with the host cell and that control the expression of the nucleic acid sequences. In particular, expression vectors of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the host cells of the present invention and can include bacterial, yeast, fungal, insect, animal, and plant transcription control sequences.

A recombinant molecule of the present invention can be any nucleic acid sequence combination herein described operatively linked to any transcription control sequence capable of effectively regulating expression of the nucleic acid sequence in the cell to be transformed.

Recombinant cells of the present invention include any cells transformed with any nucleic acid sequences of the present invention.

It may be appreciated by one skilled in the art that use of recombinant DNA technologies can improve expression of transformed nucleic acid sequences by manipulating, for example, the number of copies of the nucleic acid sequences within a host cell, the efficiency with which those nucleic acid sequences are transcribed, the efficiency with which the resultant transcripts are translated, and the efficiency of post-translational modifications. Recombinant techniques useful for increasing the expression of nucleic acid sequences encoding enzymes include, but are not limited to, operatively linking nucleic acid sequences to high-copy number plasmids, integration of the nucleic acid sequences into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Delgarno sequences), modification of the nucleic acid sequences encoding enzymes to correspond to the codon usage of the host cell, deletion of sequences that destabilize transcripts, and use of control signals that temporally separate recombinant cell growth from recombinant enzyme production during culturing. The activity of an expressed recombinant enzyme of the present invention may be improved by fragmenting, modifying, or derivatizing nucleic acid sequences encoding enzymes involved in the above-described pathways.

The foregoing description of the invention has been presented for purposes of illustration and description. Further, the description is not intended to limit the invention to the form disclosed herein. Consequently, variations and modifications commensurate with the above teachings, and the skill or knowledge in the relevant art are within the scope of the present invention. The preferred embodiment described herein above is further intended to explain the best mode known of practicing the invention and to enable others skilled in the art to utilize the invention in various embodiments and with various modifications required by their particular applications or uses of the invention. It is intended that the appended claims be construed to include alternate embodiments to the extent permitted by the prior art.

What is claimed is:

1. A substantially pure protein comprising the amino-acid sequence, as set forth in SEQ ID No. 2.

2. The protein of claim 1, wherein said protein does not contain Src homology 2 or arc homology 3 domains.

3. The protein of claim 1, wherein said protein comprises a serine and threonine rich moiety.

4. The protein of claim 1, wherein said protein comprises a kinase catalytic domain.

5. The protein of claim 1, wherein said protein is capable of activating MEK or MAPK protein.

6. The protein of claim 1, wherein said protein is encoded by a nucleic acid sequence, that encodes a protein capable of phosphorylating mammalian MEK independent of Raf protein.

7. The protein of claim 1, wherein said protein is used to produce antibodies capable of binding to MEKK protein.

8. The protein of claim 7, wherein said antibody is monoclonal.

9. A substantially pure protein encoded by the nucleic acid sequence as set forth in SEQ ID NO: 1.

10. A substantially pure MEKK protein, capable of phosphorylating mammalian MEK protein, wherein said protein comprises a serine and threonine rich moiety and a kinase catalytic domain and does not contain SH2 or SH3 domains.

11. The protein of claim 4, wherein said protein is capable of activating MEK or MAPK protein.

12. The protein of claim 4, wherein said protein comprises at least 672 amino acids.

13. The protein of claim 4, wherein said protein functions in the manner as the protein comprising the amino acid sequence shown in FIG. 1 (SEQ ID NO:1).

14. A substantially pure protein of claim 4, capable of phosphorylating MEK protein after about 40 minutes in a reaction mixture containing MgCl$_2$ and ATP, said mixture maintained at a pH of between about pH 6.0 and pH 8.0, said protein having an amino acid sequence distinct from Raf protein.

15. A substantially pure MEKK protein of claim 4, capable of regulating the activity of MAPK protein independent of Raf protein, said protein having an amino acid sequence distinct from said Raf protein.

16. A substantially pure MEKK protein of claim 1, capable of regulating signals initiated from a growth factor receptor on the surface of a cell by regulating the activity of MAPK protein, said ability to regulate being divergent from Raf protein signal regulation.

17. The protein of claim 16, wherein said growth factor receptor is coupled to heterotrimeric guanine nucleotide binding proteins.

18. The protein of claim 16, wherein said growth factor receptor is selected from the group consisting of thrombin receptors and muscarinic receptors.

19. A substantially pure MEKK protein of claim 4, which represents a divergence in mammalian cells from a yeast pheromone-responsive protein kinase system, said protein being capable of regulating MAPK protein independent of Raf protein.

* * * * *

UNITED STATES PATENT AND TRADEMARK OFFICE
CERTIFICATE OF CORRECTION

PATENT NO. : 5,405,941
DATED : April 11, 1995
INVENTOR(S) : Johnson

Page 1 of 2

It is certified that error appears in the above-identified patent and that said Letters Patent is hereby corrected as shown below:

On the title page, item [56] References Cited:

On the cover page, in the "Stevenson et al." reference, please delete "Respone" and insert therefor --Response--.
On the cover page, in the "Stevenson et al." reference, please delete "GENES" and insert therefor --Genes--.
On the cover page, in the "Tamaki et al." reference, please delete "SIgnal" and insert therefor --Signal--.
In Column 1, line 15, please delete "MED" and insert therefor --MEK--.
In Column 1, line 52, please delete "serinethreonine" and insert therefor --serine-threonine--.
In Column 4, line 4, please delete "
insert therefor --dideoxynucleotide--.
In Column 4, line 25, please delete "(SH2or" and insert --(SH2) or--.
In Column 9, line 57, please delete ",," and insert therefor --,--.
In column 25, (claim 2) line 26, please delete "arc" and insert therefor --Src--.
In column 25, (claim 11) line 50, please delete "4" and insert therefor --10--.
In column 26, (claim 12) line 20, please delete "4" and insert therefor --10--.
In column 26, (claim 13) line 22, please delete "4" and insert therefor --10--.
In column 26, (claim 14) line 25, please delete "4" and insert therefor --10--.
In column 26, (claim 15) line 31, please delete "4" and insert therefor --10--.
In column 26, (claim 16, line 35, please delete "4" and insert therefor --10--.

UNITED STATES PATENT AND TRADEMARK OFFICE
CERTIFICATE OF CORRECTION

PATENT NO. :   5,405,941
DATED      :   April 11, 1995
INVENTOR(S) :  Johnson

It is certified that error appears in the above-identified patent and that said Letters Patent is hereby corrected as shown below:

In column 26, (claim 19) line 46, please delete "4" and insert therefor --10--.

Signed and Sealed this

Eleventh Day of July, 1995

Attest:

BRUCE LEHMAN

*Attesting Officer*    *Commissioner of Patents and Trademarks*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3260 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: MEKK
        ( B ) STRAIN: murine ( v i i ) IMMEDIATE SOURCE:
        ( A ) LIBRARY: mouse liver
        ( B ) CLONE: MEKK cDNA ( i x ) FEATURE:
        ( A ) NAME/KEY: 5'UTR
        ( B ) LOCATION: 1..485

( i x ) FEATURE:
        ( A ) NAME/KEY: CDS
        ( B ) LOCATION: 486..2501

( i x ) FEATURE:
        ( A ) NAME/KEY: 3'UTR
        ( B ) LOCATION: 2502..3260

( x i ) SEQUENCE DESCRIPTION: SEQ ID NO:1:

```
TACACTCCTT  GCCACAGTCT  GGCAGAAAGA  ATCAAACTTC  AGAGACTCCT  CCGGCCAGTT        60
```

|   |   |   |   |   |   |   |   |   |   |   |   |   |   |   |   |   |
|---|---|---|---|---|---|---|---|---|---|---|---|---|---|---|---|---|
| GTAGACACTA | TCCTTGTCAA | GTGTGCAGAT | CCAACAGCCG | CACGAGTCAG | CTGTCCATAT | 120 |
| CTACAGTGCT | GGAACTCTGC | AAGGGCCAAG | CAGGAGAGCT | GGCGGTTGGG | AGAGAAATAC | 180 |
| TTAAAGCTGG | GTCCATCGGG | GTTGGTGGTG | TCGATTACGT | CTTAAGTTGT | ATCCTTGGAA | 240 |
| ACCAAGCTGA | ATCAAACAAC | TGGCAAGAAC | TGCTGGGTCG | CCTCTGTCTT | ATAGACAGGT | 300 |
| TGCTGTTGGA | ATTTCCTGCT | GAATTCTATC | CTCATATTGT | CAGTACTGAT | GTCTCACAAG | 360 |
| CTGAGCCTGT | TGAAATCAGG | TACAAGAAGC | TGCTCTCCCT | CTTAACCTTT | GCCTTGCAAT | 420 |
| CCATTGACAA | TTCCCACTCG | ATGGTTGGCA | AGCTCTCTCG | GAGGATATAT | CTGAGCTCTG | 480 |

```
CCAGG ATG GTG ACC GCA GTG CCC GCT GTG TTT TCC AAG CTG GTA ACC           527
      Met Val Thr Ala Val Pro Ala Val Phe Ser Lys Leu Val Thr
       1               5                   10

ATG CTT AAT GCT TCT GGC TCC ACC CAC TTC ACC AGG ATG CGC CGG CGT         575
Met Leu Asn Ala Ser Gly Ser Thr His Phe Thr Arg Met Arg Arg Arg
 15              20                  25                  30

CTG ATG GCT ATC GCG GAT GAG GTA GAA ATT GCC GAG GTC ATC CAG CTG         623
Leu Met Ala Ile Ala Asp Glu Val Glu Ile Ala Glu Val Ile Gln Leu
                 35                  40                  45

GGT GTG GAG GAC ACT GTG GAT GGG CAT CAG GAC AGC TTA CAG GCC GTG         671
Gly Val Glu Asp Thr Val Asp Gly His Gln Asp Ser Leu Gln Ala Val
             50                  55                  60

GCC CCC ACC AGC TGT CTA GAA AAC AGC TCC CTT GAG CAC ACA GTC CAT         719
Ala Pro Thr Ser Cys Leu Glu Asn Ser Ser Leu Glu His Thr Val His
         65                  70                  75

AGA GAG AAA ACT GGA AAA GGA CTA AGT GCT ACG AGA CTG AGT GCC AGC         767
Arg Glu Lys Thr Gly Lys Gly Leu Ser Ala Thr Arg Leu Ser Ala Ser
     80                  85                  90

TCG GAG GAC ATT TCT GAC AGA CTG GCC GGC GTC TCT GTA GGA CTT CCC         815
Ser Glu Asp Ile Ser Asp Arg Leu Ala Gly Val Ser Val Gly Leu Pro
 95                 100                 105                 110

AGC TCA ACA ACA ACA GAA CAA CCA AAG CCA GCG GTT CAA ACA AAA GGC         863
Ser Ser Thr Thr Thr Glu Gln Pro Lys Pro Ala Val Gln Thr Lys Gly
                115                 120                 125

AGA CCC CAC AGT CAG TGT TTG AAC TCC TCC CCT TTG TCT CAT GCT CAA         911
Arg Pro His Ser Gln Cys Leu Asn Ser Ser Pro Leu Ser His Ala Gln
            130                 135                 140

TTA ATG TTC CCA GCA CCA TCA GCC CCT TGT TCC TCT GCC CCG TCT GTC         959
Leu Met Phe Pro Ala Pro Ser Ala Pro Cys Ser Ser Ala Pro Ser Val
        145                 150                 155

CCA GAT ATT TCT AAG CAC AGA CCC CAG GCA TTT GTT CCC TGC AAA ATA         1007
Pro Asp Ile Ser Lys His Arg Pro Gln Ala Phe Val Pro Cys Lys Ile
    160                 165                 170

CCT TCC GCA TCT CCT CAG ACA CAG CGC AAG TTC TCT CTA CAA TTC CAG         1055
Pro Ser Ala Ser Pro Gln Thr Gln Arg Lys Phe Ser Leu Gln Phe Gln
175                 180                 185                 190

AGG AAC TGC TCT GAA CAC CGA GAC TCA GAC CAG CTC TCC CCA GTC TTC         1103
Arg Asn Cys Ser Glu His Arg Asp Ser Asp Gln Leu Ser Pro Val Phe
                195                 200                 205

ACT CAG TCA AGA CCC CCA CCC TCC AGT AAC ATA CAC AGG CCA AAG CCA         1151
Thr Gln Ser Arg Pro Pro Pro Ser Ser Asn Ile His Arg Pro Lys Pro
            210                 215                 220

TCC CGA CCC GTT CCG GGC AGT ACA AGC AAA CTA GGG GAC GCC ACA AAA         1199
Ser Arg Pro Val Pro Gly Ser Thr Ser Lys Leu Gly Asp Ala Thr Lys
        225                 230                 235

AGT AGC ATG ACA CTT GAT CTG GGC AGT GCT TCC AGG TGT GAC GAC AGC         1247
Ser Ser Met Thr Leu Asp Leu Gly Ser Ala Ser Arg Cys Asp Asp Ser
    240                 245                 250

TTT GGC GGC GGC GGC AAC AGT GGC AAC GCC GTC ATA CCC AGC GAC GAG         1295
Phe Gly Gly Gly Gly Asn Ser Gly Asn Ala Val Ile Pro Ser Asp Glu
```

```
   255                         260                         265                          270
ACA GTG TTC ACG CCG GTG GAG GAC AAG TGC AGG TTA GAT GTG AAC ACC    1343
Thr Val Phe Thr Pro Val Glu Asp Lys Cys Arg Leu Asp Val Asn Thr
            275                 280                 285

GAG CTC AAC TCC AGC ATC GAG GAC CTT CTT GAA GCA TCC ATG CCT TCA    1391
Glu Leu Asn Ser Ser Ile Glu Asp Leu Leu Glu Ala Ser Met Pro Ser
                290                 295                 300

AGT GAC ACG ACA GTC ACT TTC AAG TCC GAA GTC GCC GTC CTC TCT CCG    1439
Ser Asp Thr Thr Val Thr Phe Lys Ser Glu Val Ala Val Leu Ser Pro
        305                 310                 315

GAA AAG GCC GAA AAT GAC GAC ACC TAC AAA GAC GAC GTC AAT CAT AAT    1487
Glu Lys Ala Glu Asn Asp Asp Thr Tyr Lys Asp Asp Val Asn His Asn
    320                 325                 330

CAA AAG TGC AAA GAA AAG ATG GAA GCT GAA GAG GAG GAG GCT TTA GCG    1535
Gln Lys Cys Lys Glu Lys Met Glu Ala Glu Glu Glu Glu Ala Leu Ala
335                 340                 345                 350

ATC GCC ATG GCG ATG TCA GCG TCT CAG GAT GCC CTC CCC ATC GTC CCT   1583
 Ile Ala Met Ala Met Ser Ala Ser Gln Asp Ala Leu Pro Ile Val Pro
                 355                 360                 365

CAG CTG CAG GTG GAA AAT GGA GAA GAT ATT ATC ATC ATT CAG CAG GAC    1631
Gln Leu Gln Val Glu Asn Gly Glu Asp Ile Ile Ile Ile Gln Gln Asp
             370                 375                 380

ACA CCA GAA ACT CTT CCA GGA CAT ACC AAA GCG AAA CAG CCT TAC AGA    1679
Thr Pro Glu Thr Leu Pro Gly His Thr Lys Ala Lys Gln Pro Tyr Arg
         385                 390                 395

GAA GAC GCT GAG TGG CTG AAA GGC CAG CAG ATA GGC CTC GGA GCA TTT    1727
Glu Asp Ala Glu Trp Leu Lys Gly Gln Gln Ile Gly Leu Gly Ala Phe
     400                 405                 410

TCT TCC TGT TAC CAA GCA CAG GAT GTG GGG ACT GGG ACT TTA ATG GCT    1775
Ser Ser Cys Tyr Gln Ala Gln Asp Val Gly Thr Gly Thr Leu Met Ala
415                 420                 425                 430

GTG AAA CAG GTG ACG TAC GTC AGA AAC ACA TCC TCC GAG CAG GAG GAG    1823
Val Lys Gln Val Thr Tyr Val Arg Asn Thr Ser Ser Glu Gln Glu Glu
                435                 440                 445

GTG GTG GAA GCG TTG AGG GAA GAG ATC CGG ATG ATG GGT CAC CTC AAC    1871
Val Val Glu Ala Leu Arg Glu Glu Ile Arg Met Met Gly His Leu Asn
            450                 455                 460

CAT CCA AAC ATC ATC CGG ATG CTG GGG GCC ACG TGC GAG AAG AGC AAC    1919
His Pro Asn Ile Ile Arg Met Leu Gly Ala Thr Cys Glu Lys Ser Asn
        465                 470                 475

TAC AAC CTC TTC ATT GAG TGG ATG GCG GGA GGA TCT GTG GCT CAC CTC    1967
Tyr Asn Leu Phe Ile Glu Trp Met Ala Gly Gly Ser Val Ala His Leu
    480                 485                 490

TTG AGT AAA TAC GGA GCT TTC AAG GAG TCA GTC GTC ATT AAC TAC ACT    2015
Leu Ser Lys Tyr Gly Ala Phe Lys Glu Ser Val Val Ile Asn Tyr Thr
495                 500                 505                 510

GAG CAG TTA CTG CGT GGC CTT TCC TAT CTC CAC GAG AAC CAG ATC ATT    2063
Glu Gln Leu Leu Arg Gly Leu Ser Tyr Leu His Glu Asn Gln Ile Ile
                515                 520                 525

CAC AGA GAC GTC AAA GGT GCC AAC CTG CTC ATT GAC AGC ACC GGT CAG    2111
His Arg Asp Val Lys Gly Ala Asn Leu Leu Ile Asp Ser Thr Gly Gln
            530                 535                 540

AGG CTG AGA ATT GCA GAC TTT GGA GCT GCT GCC AGG TTG GCA TCA AAA    2159
Arg Leu Arg Ile Ala Asp Phe Gly Ala Ala Ala Arg Leu Ala Ser Lys
        545                 550                 555

GGA ACC GGT GCA GGA GAG TTC CAG GGA CAG TTA CTG GGG ACA ATT GCA    2207
Gly Thr Gly Ala Gly Glu Phe Gln Gly Gln Leu Leu Gly Thr Ile Ala
    560                 565                 570

TTC ATG GCG CCT GAG GTC CTA AGA GGT CAG CAG TAT GGT AGG AGC TGT    2255
Phe Met Ala Pro Glu Val Leu Arg Gly Gln Gln Tyr Gly Arg Ser Cys
575                 580                 585                 590
```

|  |  |  |  |  |  |  |  |  |  |  |  |  |  |  |  |
|---|---|---|---|---|---|---|---|---|---|---|---|---|---|---|---|
| GAT | GTA | TGG | AGT | GTT | GGC | TGC | GCC | ATT | ATA | GAA | ATG | GCT | TGT | GCA | AAA |
| Asp | Val | Trp | Ser | Val | Gly | Cys | Ala | Ile | Ile | Glu | Met | Ala | Cys | Ala | Lys |
|  |  |  | 595 |  |  |  |  | 600 |  |  |  |  | 605 |  |  |

2303

|  |  |  |  |  |  |  |  |  |  |  |  |  |  |  |  |
|---|---|---|---|---|---|---|---|---|---|---|---|---|---|---|---|
| CCA | CCT | TGG | AAT | GCA | GAA | AAA | CAC | TCC | AAT | CAT | CTC | GCC | TTG | ATA | TTT |
| Pro | Pro | Trp | Asn | Ala | Glu | Lys | His | Ser | Asn | His | Leu | Ala | Leu | Ile | Phe |
|  |  |  | 610 |  |  |  |  | 615 |  |  |  |  | 620 |  |  |

2351

|  |  |  |  |  |  |  |  |  |  |  |  |  |  |  |  |
|---|---|---|---|---|---|---|---|---|---|---|---|---|---|---|---|
| AAG | ATT | GCT | AGC | GCA | ACT | ACT | GCA | CCG | TCC | ATC | CCG | TCA | CAC | CTG | TCC |
| Lys | Ile | Ala | Ser | Ala | Thr | Thr | Ala | Pro | Ser | Ile | Pro | Ser | His | Leu | Ser |
|  |  | 625 |  |  |  |  | 630 |  |  |  |  | 635 |  |  |  |

2399

|  |  |  |  |  |  |  |  |  |  |  |  |  |  |  |  |
|---|---|---|---|---|---|---|---|---|---|---|---|---|---|---|---|
| CCG | GGT | CTG | CGC | GAC | GTG | GCC | GTG | CGC | TGC | TTA | GAA | CTT | CAG | CCT | CAG |
| Pro | Gly | Leu | Arg | Asp | Val | Ala | Val | Arg | Cys | Leu | Glu | Leu | Gln | Pro | Gln |
|  | 640 |  |  |  |  | 645 |  |  |  |  | 650 |  |  |  |  |

2447

|  |  |  |  |  |  |  |  |  |  |  |  |  |  |  |  |
|---|---|---|---|---|---|---|---|---|---|---|---|---|---|---|---|
| GAC | CGG | CCT | CCG | TCC | AGA | GAG | CTG | CTG | AAA | CAT | CCG | GTC | TTC | CGT | ACC |
| Asp | Arg | Pro | Pro | Ser | Arg | Glu | Leu | Leu | Lys | His | Pro | Val | Phe | Arg | Thr |
| 655 |  |  |  |  | 660 |  |  |  |  | 665 |  |  |  |  | 670 |

2495

```
ACG TGG TAGTTAATTG TTCAGATCAG CTCTAATGGA GACAGGATAT CGAACCGGGA        2551
Thr Trp

GAGAGAAAAG AGAACTTGTG GGCGACCATG CCGCTAACCG CAGCCCTCAC GCCACTGAAC     2611

AGCCAGAAAC GGGGCCAGCG GGAACCGTA CCTAAGCATG TGATTGACAA ATCATGACCT      2671

GTACCTAAGC TCGATATGCA GACATCTACA GCTCGTGCAG GAACTGCACA CCGTGCCTTT    2731

CACAGGACTG GCTCTGGGGG ACCAGGAAGG CGATGGAGTT TGCATGACTA AGAACAGAA      2791

GCATAAATTT ATTTTGGAG CACTTTTTCA GCTAATCAGT ATTACCATGT ACATCAACAT      2851

GCCCGCCACA TTTCAAACTC AGACTGTCCC AGATGTCAAG ATCCACTGTG TTTGAGTTTG    2911

TTTGCAGTTC CCTCAGCTTG CTGGTAATTG TGGTGTTTTG TTTTCGATGC AAATGTGATG   2971

TAATATTCTT ATTTTCTTTG GATCAAAGCT GGACTGAAAA TTGTACTGTG TAATTATTTT   3031

TGTGTTTTTA ATGTTATTTG GTACTCGAAT TGTAAATAAC GTCTACTGCT GTTTATTCCA   3091

GTTTCTACTA CCTCAGGTGT CCTATAGATT TTTCTTCTAC CAAAGTTCAC TCTCAGAATG    3151

AAATTCTACG TGCTGTGTGA CTATGACTCC TAAGACTTCC AGGGCTTAAG GGCTAACTCC    3211

TATTAGCACC TTACTATGTA AGCAAATGCT ACAAAAAAAA AAAAAAAA                 3260
```

( 2 ) INFORMATION FOR SEQ ID NO:2:

( i ) SEQUENCE CHARACTERISTICS:
        ( A ) LENGTH: 672 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

|  |  |  |  |  |  |  |  |  |  |  |  |  |  |  |
|---|---|---|---|---|---|---|---|---|---|---|---|---|---|---|
| Met | Val | Thr | Ala | Val | Pro | Ala | Val | Phe | Ser | Lys | Leu | Val | Thr | Met | Leu |
| 1 |  |  |  | 5 |  |  |  |  | 10 |  |  |  |  | 15 |  |
| Asn | Ala | Ser | Gly | Ser | Thr | His | Phe | Thr | Arg | Met | Arg | Arg | Arg | Leu | Met |
|  |  |  | 20 |  |  |  |  | 25 |  |  |  | 30 |  |  |  |
| Ala | Ile | Ala | Asp | Glu | Val | Glu | Ile | Ala | Glu | Val | Ile | Gln | Leu | Gly | Val |
|  |  | 35 |  |  |  |  | 40 |  |  |  |  | 45 |  |  |  |
| Glu | Asp | Thr | Val | Asp | Gly | His | Gln | Asp | Ser | Leu | Gln | Ala | Val | Ala | Pro |
|  | 50 |  |  |  |  | 55 |  |  |  |  | 60 |  |  |  |  |
| Thr | Ser | Cys | Leu | Glu | Asn | Ser | Ser | Leu | Glu | His | Thr | Val | His | Arg | Glu |
| 65 |  |  |  |  | 70 |  |  |  |  | 75 |  |  |  |  | 80 |
| Lys | Thr | Gly | Lys | Gly | Leu | Ser | Ala | Thr | Arg | Leu | Ser | Ala | Ser | Ser | Glu |
|  |  |  |  | 85 |  |  |  |  | 90 |  |  |  |  | 95 |  |
| Asp | Ile | Ser | Asp | Arg | Leu | Ala | Gly | Val | Ser | Val | Gly | Leu | Pro | Ser | Ser |
|  |  |  | 100 |  |  |  |  | 105 |  |  |  |  | 110 |  |  |
| Thr | Thr | Thr | Glu | Gln | Pro | Lys | Pro | Ala | Val | Gln | Thr | Lys | Gly | Arg | Pro |
|  |  |  | 115 |  |  |  |  | 120 |  |  |  |  | 125 |  |  |

```
His  Ser  Gln  Cys  Leu  Asn  Ser  Ser  Pro  Leu  Ser  His  Ala  Gln  Leu  Met
     130                 135                      140

Phe  Pro  Ala  Pro  Ser  Ala  Pro  Cys  Ser  Ser  Ala  Pro  Ser  Val  Pro  Asp
145                      150                      155                      160

Ile  Ser  Lys  His  Arg  Pro  Gln  Ala  Phe  Val  Pro  Cys  Lys  Ile  Pro  Ser
               165                      170                      175

Ala  Ser  Pro  Gln  Thr  Gln  Arg  Lys  Phe  Ser  Leu  Gln  Phe  Gln  Arg  Asn
               180                      185                      190

Cys  Ser  Glu  His  Arg  Asp  Ser  Asp  Gln  Leu  Ser  Pro  Val  Phe  Thr  Gln
          195                      200                      205

Ser  Arg  Pro  Pro  Pro  Ser  Ser  Asn  Ile  His  Arg  Pro  Lys  Pro  Ser  Arg
     210                      215                      220

Pro  Val  Pro  Gly  Ser  Thr  Ser  Lys  Leu  Gly  Asp  Ala  Thr  Lys  Ser  Ser
225                      230                      235                      240

Met  Thr  Leu  Asp  Leu  Gly  Ser  Ala  Ser  Arg  Cys  Asp  Asp  Ser  Phe  Gly
               245                      250                      255

Gly  Gly  Gly  Asn  Ser  Gly  Asn  Ala  Val  Ile  Pro  Ser  Asp  Glu  Thr  Val
               260                      265                      270

Phe  Thr  Pro  Val  Glu  Asp  Lys  Cys  Arg  Leu  Asp  Val  Asn  Thr  Glu  Leu
          275                      280                      285

Asn  Ser  Ser  Ile  Glu  Asp  Leu  Leu  Glu  Ala  Ser  Met  Pro  Ser  Ser  Asp
     290                      295                      300

Thr  Thr  Val  Thr  Phe  Lys  Ser  Glu  Val  Ala  Val  Leu  Ser  Pro  Glu  Lys
305                      310                      315                      320

Ala  Glu  Asn  Asp  Asp  Thr  Tyr  Lys  Asp  Asp  Val  Asn  His  Asn  Gln  Lys
               325                      330                      335

Cys  Lys  Glu  Lys  Met  Glu  Ala  Glu  Glu  Glu  Ala  Leu  Ala  Ile  Ala
               340                      345                      350

Met  Ala  Met  Ser  Ala  Ser  Gln  Asp  Ala  Leu  Pro  Ile  Val  Pro  Gln  Leu
          355                      360                      365

Gln  Val  Glu  Asn  Gly  Glu  Asp  Ile  Ile  Ile  Ile  Gln  Gln  Asp  Thr  Pro
     370                      375                      380

Glu  Thr  Leu  Pro  Gly  His  Thr  Lys  Ala  Lys  Gln  Pro  Tyr  Arg  Glu  Asp
385                      390                      395                      400

Ala  Glu  Trp  Leu  Lys  Gly  Gln  Gln  Ile  Gly  Leu  Gly  Ala  Phe  Ser  Ser
               405                      410                      415

Cys  Tyr  Gln  Ala  Gln  Asp  Val  Gly  Thr  Gly  Thr  Leu  Met  Ala  Val  Lys
               420                      425                      430

Gln  Val  Thr  Tyr  Val  Arg  Asn  Thr  Ser  Ser  Glu  Gln  Glu  Glu  Val  Val
          435                      440                      445

Glu  Ala  Leu  Arg  Glu  Glu  Ile  Arg  Met  Met  Gly  His  Leu  Asn  His  Pro
450                      455                      460

Asn  Ile  Ile  Arg  Met  Leu  Gly  Ala  Thr  Cys  Glu  Lys  Ser  Asn  Tyr  Asn
465                      470                      475                      480

Leu  Phe  Ile  Glu  Trp  Met  Ala  Gly  Gly  Ser  Val  Ala  His  Leu  Leu  Ser
               485                      490                      495

Lys  Tyr  Gly  Ala  Phe  Lys  Glu  Ser  Val  Val  Ile  Asn  Tyr  Thr  Glu  Gln
               500                      505                      510

Leu  Leu  Arg  Gly  Leu  Ser  Tyr  Leu  His  Glu  Asn  Gln  Ile  Ile  His  Arg
          515                      520                      525

Asp  Val  Lys  Gly  Ala  Asn  Leu  Leu  Ile  Asp  Ser  Thr  Gly  Gln  Arg  Leu
          530                      535                      540

Arg  Ile  Ala  Asp  Phe  Gly  Ala  Ala  Arg  Leu  Ala  Ser  Lys  Gly  Thr
545                      550                      555                      560
```

```
Gly Ala Gly Glu Phe Gln Gly Gln Leu Leu Gly Thr Ile Ala Phe Met
                565             570                 575

Ala Pro Glu Val Leu Arg Gly Gln Gln Tyr Gly Arg Ser Cys Asp Val
            580             585             590

Trp Ser Val Gly Cys Ala Ile Ile Glu Met Ala Cys Ala Lys Pro Pro
        595                 600             605

Trp Asn Ala Glu Lys His Ser Asn His Leu Ala Leu Ile Phe Lys Ile
    610             615                 620

Ala Ser Ala Thr Thr Ala Pro Ser Ile Pro Ser His Leu Ser Pro Gly
625                     630             635                 640

Leu Arg Asp Val Ala Val Arg Cys Leu Glu Leu Gln Pro Gln Asp Arg
            645                 650             655

Pro Pro Ser Arg Glu Leu Leu Lys His Pro Val Phe Arg Thr Thr Trp
            660             665                 670
```